(12) United States Patent
Tahara et al.

(10) Patent No.: US 10,006,860 B2
(45) Date of Patent: Jun. 26, 2018

(54) DIGITAL HOLOGRAPHY RECORDING DEVICE, DIGITAL HOLOGRAPHY PLAYBACK DEVICE, DIGITAL HOLOGRAPHY RECORDING METHOD, AND DIGITAL HOLOGRAPHY PLAYBACK METHOD

(71) Applicants: The School Corporation Kansai University, Suita-shi, Osaka (JP); Inter-University Research Institute Corporation Research Organization of Information and Systems, Tachikawa-shi, Tokyo (JP)

(72) Inventors: Tatsuki Tahara, Suita (JP); Imari Sato, Tokyo (JP); Yuki Takahashi, Suita (JP); Takeya Kanno, Suita (JP)

(73) Assignees: The School Corporation Kansai University, Suita, Osaka (JP); Inter-University Research Institute Corporation Research Organization of Information and Systems, Tachikawa, Tokyo (JP)

( * ) Notice: Subject to any disclaimer, the term of this patent is extended or adjusted under 35 U.S.C. 154(b) by 0 days. days.

(21) Appl. No.: 15/546,651

(22) PCT Filed: Jan. 28, 2016

(86) PCT No.: PCT/JP2016/052487
§ 371 (c)(1),
(2) Date: Jul. 26, 2017

(87) PCT Pub. No.: WO2016/121866
PCT Pub. Date: Aug. 4, 2016

(65) Prior Publication Data
US 2018/0011022 A1 Jan. 11, 2018

(30) Foreign Application Priority Data
Jan. 28, 2015 (JP) .................. 2015-014802

(51) Int. Cl.
*G01N 21/64* (2006.01)
*G03H 1/22* (2006.01)
*G01H 1/06* (2006.01)

(52) U.S. Cl.
CPC ............... *G01N 21/64* (2013.01); *G01H 1/06* (2013.01); *G03H 1/22* (2013.01)

(58) Field of Classification Search
CPC .. G01N 21/6458; G02B 21/16; G02B 21/365; G03H 1/0005; G03H 1/0866;
(Continued)

(56) References Cited

U.S. PATENT DOCUMENTS

| 7,217,573 B1 | 5/2007 | Oshida et al. |
| 8,736,823 B2 * | 5/2014 | Pfaff .................... G01R 15/241 356/35.5 |

(Continued)

FOREIGN PATENT DOCUMENTS

| JP | 2002-055050 A | 2/2002 |
| JP | 2002-072835 A | 3/2002 |

(Continued)

OTHER PUBLICATIONS

Indebetouw et al., "Quantitative phase imaging with scanning holographic microscopy: an experimental assesment," 2006, BioMedical Engineering OnLine, vol. 5, No. 63, 7 pages.*

(Continued)

*Primary Examiner* — Kiho Kim
(74) *Attorney, Agent, or Firm* — Mintz Levin Cohn Ferris Glovsky and Popeo, P.C.; David G. Conlin; Steven M. Jensen

(57) ABSTRACT

Both a hologram and fluorescence are simultaneously captured in a state in which they can be reconstructed separately. A recording device (10) includes: a laser light source (LS1) which irradiates a subject (13) with object illumination light
(Continued)

so that object light is generated; and an image capturing device (12) which captures (i) a hologram formed by interference between reference light and object light and (ii) an image of fluorescence, and the object illumination light further excites a fluorescent material (14) contained in the subject (13).

17 Claims, 21 Drawing Sheets

(58) Field of Classification Search
CPC ..... G03H 2001/005; G03H 2001/0456; G03H 2001/0458; G03H 2222/24; G03H 2223/26; G03H 1/041
See application file for complete search history.

(56) References Cited

U.S. PATENT DOCUMENTS

| | | | |
|---|---|---|---|
| 2004/0156098 A1* | 8/2004 | Dubois | G01N 21/6458 359/368 |
| 2005/0006597 A1 | 1/2005 | Wolleschensky et al. | |
| 2008/0225906 A1 | 9/2008 | Ishihara et al. | |
| 2012/0200901 A1 | 8/2012 | Dubois et al. | |
| 2012/0218379 A1 | 8/2012 | Ozcan et al. | |
| 2012/0283530 A1 | 11/2012 | Maynard et al. | |
| 2013/0057935 A1 | 3/2013 | Joo | |

FOREIGN PATENT DOCUMENTS

| | | |
|---|---|---|
| JP | 2004-538451 A | 12/2004 |
| JP | 2005-037388 A | 2/2005 |
| JP | 2008-225013 A | 9/2008 |
| JP | 2011-185757 A | 9/2011 |
| JP | 2013-054336 A | 3/2013 |
| JP | 2013-507647 A | 3/2013 |
| JP | 2013-508775 A | 3/2013 |
| JP | 2013-511341 A | 4/2013 |
| JP | 2015-001726 A | 1/2015 |

OTHER PUBLICATIONS

Maschio et al., "Simultaneous two-photon imaging and photostimulation with structured ligth illumination," 2010, Optics Express, vol. 18, No. 18, pp. 18720-18731.*

Rosen et al., "Fluorescence incoherent color holography," 2007, Optics Express, vol. 15, No. 5, pp. 2244-2250.*

Rosen et al., "Non-scanning motionless fluorescence three-dimensional holographic microscopy," 2008, Nature Photonics, vol. 2, pp. 190-195.*

X. Quan et al., "Phase and fluorescence imaging by combination of digital holographic microscopy and fluorescence microscopy," v. 22, 2015, pp. 349-353, Optical Review.

International Search Report for PCT/JP2016/062487 (dated Apr. 2016).

International Preliminary Report on Patentability for PCT/JP2016/052487 (dated Aug. 3, 2017).

* cited by examiner

Image seen through normal camera

Recorded image

Recorded image — Zeroth-order diffracted light component $(|O|^2 + |R|^2)$ (a) Fourier-transformed image (b) Fluorescence image (Reconstruction)

(a) R channel reflected light image
(b) G channel reflected light image
(c) B channel reflected light image
(d) Reflected light image (Color composition)

Height distribution

Image seen through normal camera

| 0 | $\pi/2$ | $\pi$ | $3\pi/2$ |
|---|---|---|---|
| $\pi/2$ | $\pi$ | $3\pi/2$ | 0 |
| $\pi$ | $3\pi/2$ | 0 | $\pi/2$ |
| $3\pi/2$ | 0 | $\pi/2$ | $\pi$ |

Recorded image

Phase shift method
(a) Reflected light image (Reconstruction)
(b) Phase distribution Phase shift method Fluorescence image
(Reconstruction)

DIGITAL HOLOGRAPHY RECORDING DEVICE, DIGITAL HOLOGRAPHY PLAYBACK DEVICE, DIGITAL HOLOGRAPHY RECORDING METHOD, AND DIGITAL HOLOGRAPHY PLAYBACK METHOD

CROSS-REFERENCE TO RELATED APPLICATIONS

This application is a National Phase application filed under 35 USC 371 of PCT International Application No. PCT/JP2016/052487 with an International Filing Date of Jan. 28, 2016, which claims under 35 U.S.C. § 119(a) the benefit of Japanese Application No. 2015-014802, filed Jan. 28, 2015, the entire contents of which are incorporated herein by reference.

TECHNICAL FIELD

The present invention relates to a digital holography apparatus and a digital holography method.

BACKGROUND ART

In the following descriptions, radian is used as a unit for phases. An interferometric technique using interference of light, particularly digital holography, is one of recently attractive measurement methods because of its feature of enabling three-dimensional information of an object to be obtained in a noncontact and nondestructive manner.

Digital holography is a technology in which an image of a three-dimensional object is reconstructed by use of a computer on the basis of interference fringes obtained by irradiation of the three-dimensional object with light. Generally, for example, interference fringes formed by (i) object light obtained by irradiation of a three-dimensional object with light and (ii) reference light which is coherent with respect to the object light are recorded by use of an image capturing element such as a CCD (charge coupled device) or a CMOS (complementary metal oxide semiconductor). The image of the three-dimensional object is reconstructed by a computer on the basis of the recorded interference fringes.

Patent Literature 1 discloses a technique of performing a measurement and recording step of sequentially and separately measuring and recording an interferometer signal obtained by digital holography and a fluorescence signal from a sample and a step of combining the interferometer signal and the fluorescence signal in order to reconfigure the three-dimensional image.

Patent Literature 2 discloses a technique of optically detecting fluorescence from an object.

Patent Literature 3 discloses a technique of measuring a polarized light component of fluorescence emitted by a sample.

Patent Literatures 4 to 7 each disclose a technique employing fluorescence detection.

CITATION LIST

Patent Literature

[Patent Literature 1]
Published Japanese Translation of PCT International Application, Tokuhyo, No. 2004-538451 (Publication date: Dec. 24, 2004)

[Patent Literature 2]
Japanese Patent Application Publication Tokukai No. 2005-037388 (Publication date: Feb. 10, 2005)

[Patent Literature 3]
Japanese Patent Application Publication Tokukai No. 2008-225013 (Publication date: Sep. 25, 2008)

[Patent Literature 4]
Japanese Patent Application Publication Tokukai No. 2002-055050 (Publication date: Feb. 20, 2002)

[Patent Literature 5]
Japanese Patent Application Publication Tokukai No. 2002-072835 (Publication date: Mar. 12, 2002)

[Patent Literature 6]
Japanese Patent Application Publication Tokukai No. 2011-185757 (Publication date: Sep. 22, 2011)

[Patent Literature 7]
Published Japanese Translation of PCT International Application, Tokuhyo, No. 2013-511341 (Publication date: Apr. 4, 2013)

SUMMARY OF INVENTION

Technical Problem

The conventional techniques, however, separately capture (i) a hologram corresponding to object light containing three-dimensional shape information of the object and (ii) fluorescence. For example, at a first time, the object light is generated from the object by use of a laser light source, and the hologram formed by interference between the object light and the reference light is captured. Next, at a second time, the laser light source is turn off, fluorescence is generated from the object by use of an excitation light source, and only fluorescence is imaged. Thus, in the conventional techniques, the hologram and the fluorescence are captured separately by use of individual light sources. Therefore, it is impossible to capture a moving image of both a hologram and fluorescence at a frame rate of a camera.

In an aspect of the present invention, it is possible to simultaneously capture both a hologram and fluorescence in a state in which they can be reconstructed separately.

Solution to Problem

A digital holography recording device in accordance with an embodiment of the present invention includes: a light source which irradiates an object with object illumination light so that object light is generated; and an image capturing device which captures (i) a hologram formed by interference between reference light and the object light and (ii) an image of fluorescence, the object illumination light further exciting a fluorescent material contained in the object.

A digital holography recording device in accordance with an embodiment of the present invention includes: a light source which irradiates an object with object illumination light; and an image capturing device which captures a superimposed image in which (i) a hologram formed by interference between reference light and object light from the object and (ii) an image of fluorescence emitted by a fluorescent material contained in the object are superimposed.

A digital holography reconstruction device in accordance with an embodiment of the present invention operates to: use a spatial phase shift method to determine a complex amplitude of object light based on a superimposed image in which (i) a hologram formed by interference between reference light and the object light and (ii) an image of incoherent light are superimposed; determine an intensity of the hologram based on the complex amplitude of the object light; and remove the hologram from the superimposed image to obtain the image of the incoherent light.

A digital holography reconstruction device in accordance with an embodiment of the present invention operates to: subject, to Fourier transform, a superimposed image in which (i) a hologram formed by interference between reference light and object light and (ii) an image of incoherent light are superimposed; extract a spatial spectrum of the object light from a Fourier-transformed image; subject the extracted spatial spectrum of the object light to inverse Fourier transform to determine a complex amplitude of the object light; determine a zeroth-order diffracted light component based on the complex amplitude of the object light and then remove the zeroth-order diffracted light component from the Fourier-transformed image; and extract, from the Fourier-transformed image from which the zeroth-order diffracted light component has been removed, a spatial spectrum of the image of the incoherent light.

A digital holography reconstruction device in accordance with an embodiment of the present invention operates to: subject, to Fourier transform, a superimposed image in which (i) a hologram formed by interference between reference light and object light and (ii) an image of incoherent light are superimposed; extract a spatial spectrum of the object light from a Fourier-transformed image; subject the extracted spatial spectrum of the object light to inverse Fourier transform to determine a complex amplitude of the object light; and determine an intensity of the hologram based on the complex amplitude of the object light and then remove the hologram from the superimposed image to obtain the image of the incoherent light.

A digital holography recording method in accordance with an embodiment of the present invention includes the steps of: irradiating an object with object illumination light emitted from a light source so that object light is generated and exciting a fluorescent material contained in the object with the object illumination light; and capturing (i) a hologram formed by interference between reference light and the object light and (ii) an image of fluorescence emitted by the fluorescent material.

A digital holography recording method in accordance with an embodiment of the present invention includes the steps of: irradiating an object with object illumination light; and capturing a superimposed image in which (i) a hologram formed by interference between reference light and object light from the object and (ii) an image of fluorescence emitted by a fluorescent material contained in the object are superimposed.

A digital holography reconstruction method in accordance with an embodiment of the present invention includes the steps of: using a spatial phase shift method to determine a complex amplitude of object light based on a superimposed image in which (i) a hologram formed by interference between reference light and the object light and (ii) an image of incoherent light are superimposed; determining an intensity of the hologram based on the complex amplitude of the object light; and removing the hologram from the superimposed image to obtain the image of the incoherent light.

A digital holography reconstruction method in accordance with an embodiment of the present invention includes the steps of: subjecting, to Fourier transform, a superimposed image in which (i) a hologram formed by interference between reference light and object light and (ii) an image of incoherent light are superimposed; extracting a spatial spectrum of the object light from a Fourier-transformed image; subjecting the extracted spatial spectrum of the object light to inverse Fourier transform to determine a complex amplitude of the object light; determining a zeroth-order diffracted light component based on the complex amplitude of the object light and then removing the zeroth-order diffracted light component from the Fourier-transformed image; and extracting, from the Fourier-transformed image from which the zeroth-order diffracted light component has been removed, a spatial spectrum of the image of the incoherent light.

A digital holography reconstruction method in accordance with an embodiment of the present invention includes the steps of: subjecting, to Fourier transform, a superimposed image in which (i) a hologram formed by interference between reference light and object light and (ii) an image of incoherent light are superimposed; extracting a spatial spectrum of the object light from a Fourier-transformed image; subjecting the extracted spatial spectrum of the object light to inverse Fourier transform to determine a complex amplitude of the object light; and determining an intensity of the hologram based on the complex amplitude of the object light and then removing the hologram from the superimposed image to obtain the image of the incoherent light.

Advantageous Effects of Invention

According to an aspect of the present invention, it is possible to simultaneously capture both a hologram and an image of fluorescence in a state in which they can be reconstructed separately.

According to an aspect of the present invention, it is possible to separately reconstruct object light and an image of fluorescence based on a superimposed image in which a hologram and the image of the fluorescence are superimposed.

Figure 9:
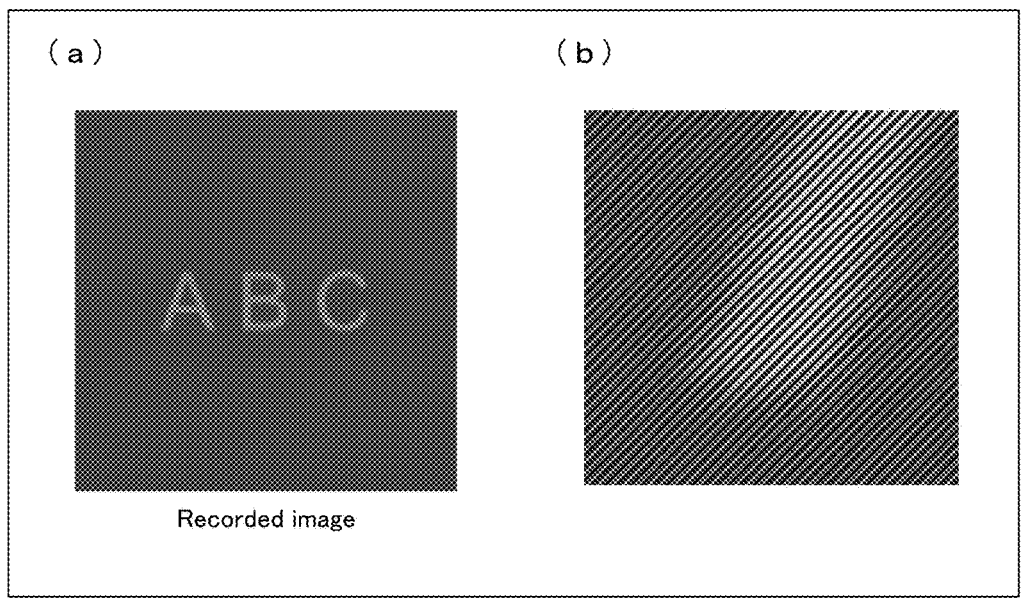

(a) of FIG. 9 shows a recorded image in the simulation, and (b) of FIG. 9 shows an enlarged part of the recorded image.

Figure 10:
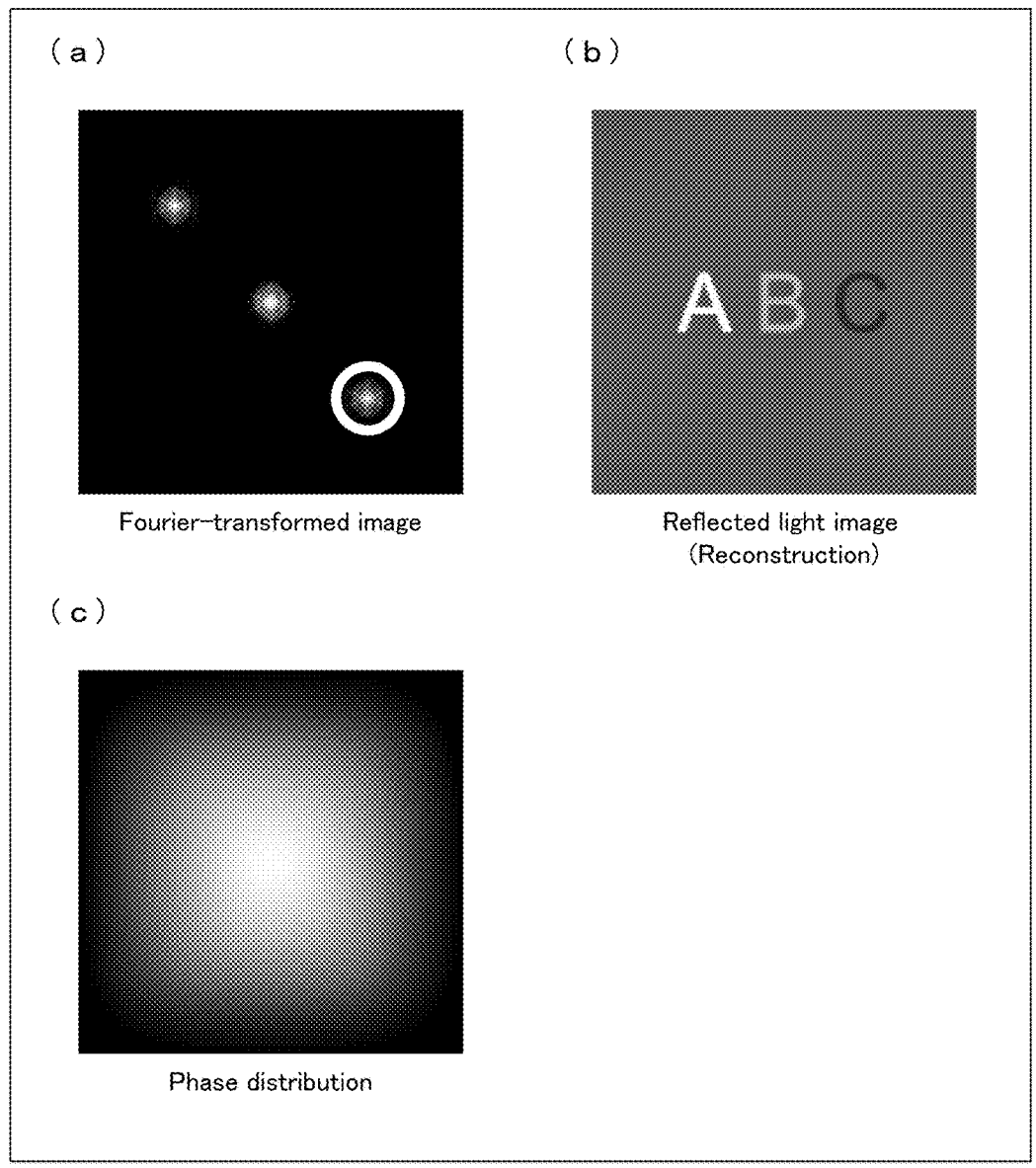

(a) of FIG. 10 shows a Fourier-transformed image, (b) of FIG. 10 shows a reconstructed reflected light image, and (c) of FIG. 10 shows a reconstructed phase distribution.

Figure 11:
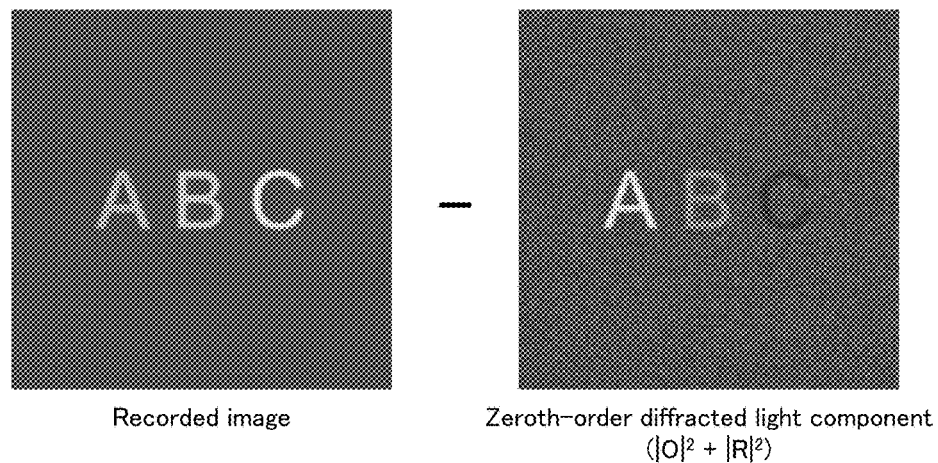

FIG. 11 shows a state in which a zeroth-order diffracted light component is subtracted from the recorded image.

Figure 12:
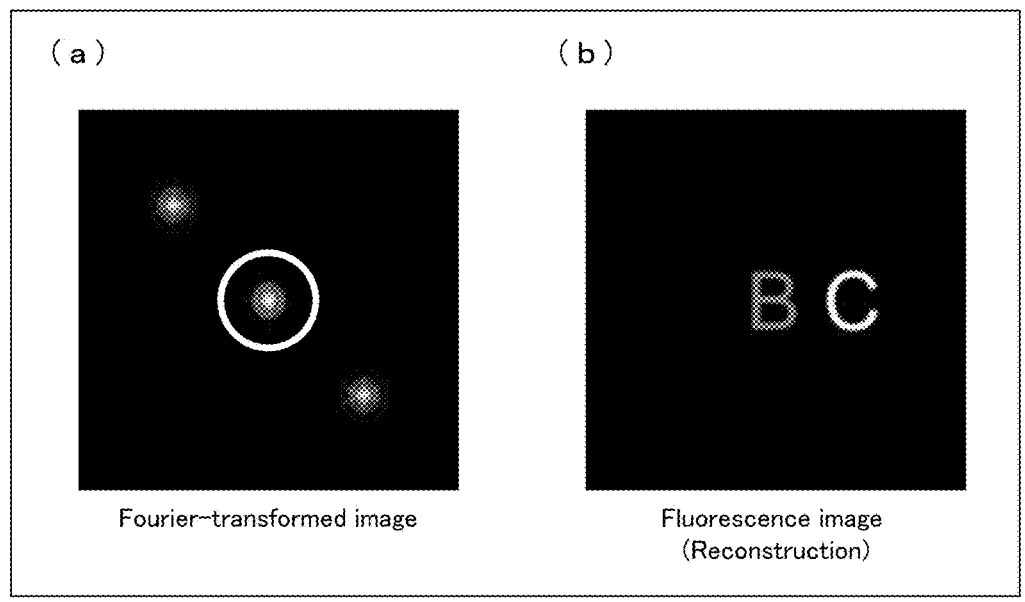

(a) of FIG. 12 shows a Fourier-transformed image in which the zeroth-order diffracted light component is removed, and (b) of FIG. 12 shows a reconstructed fluorescence image.

Figure 13:
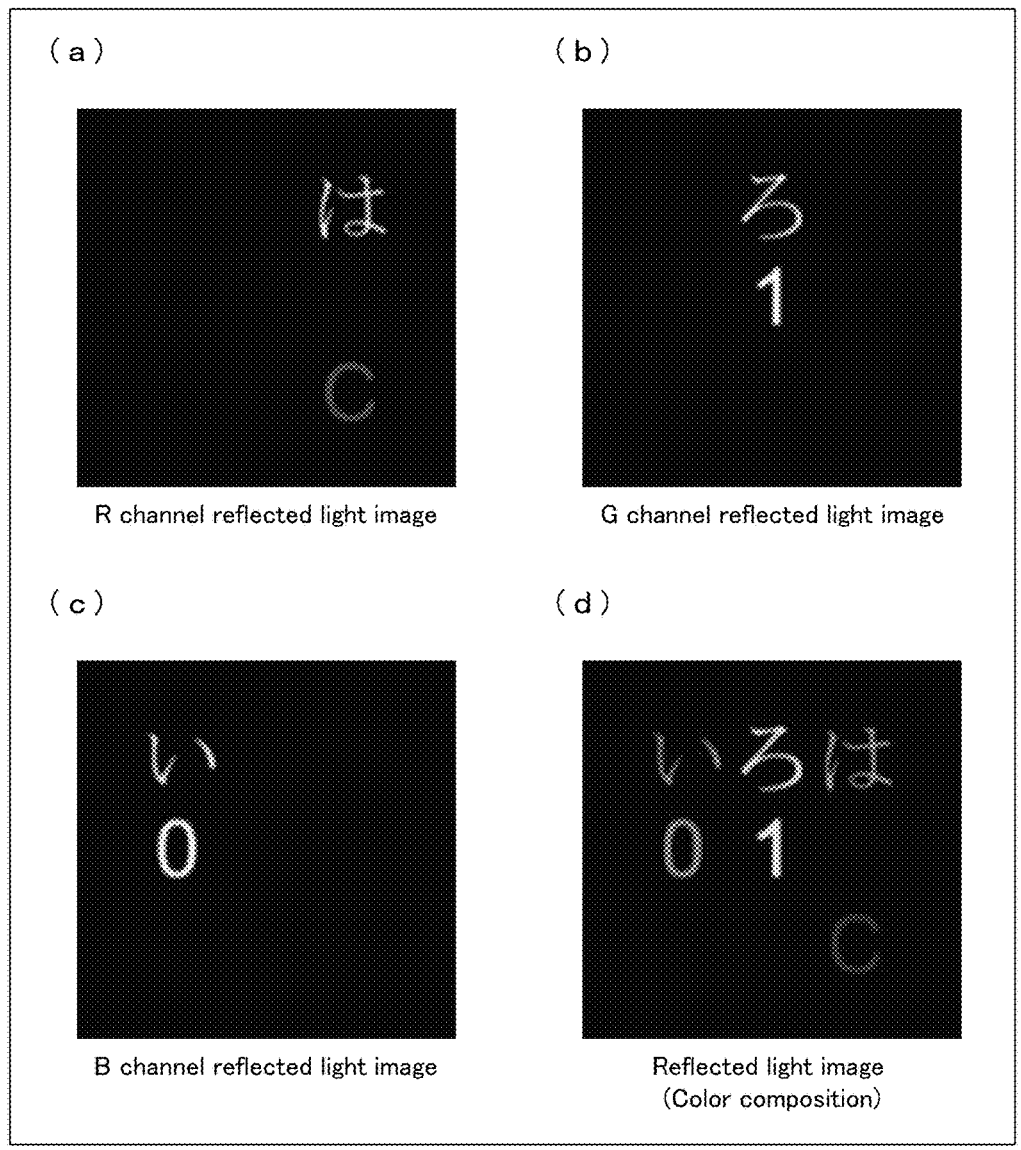

(a) of FIG. 13 shows a R channel image of reflected light of a subject used in a simulation based on still another embodiment of the present invention, (b) of FIG. 13 shows a G channel image of reflected light of the subject, (c) of FIG. 13 shows a B channel image of reflected light of the subject, and (d) of FIG. 13 shows a reflected light image, of the subject, obtained by RGB color composition.

Figure 14:
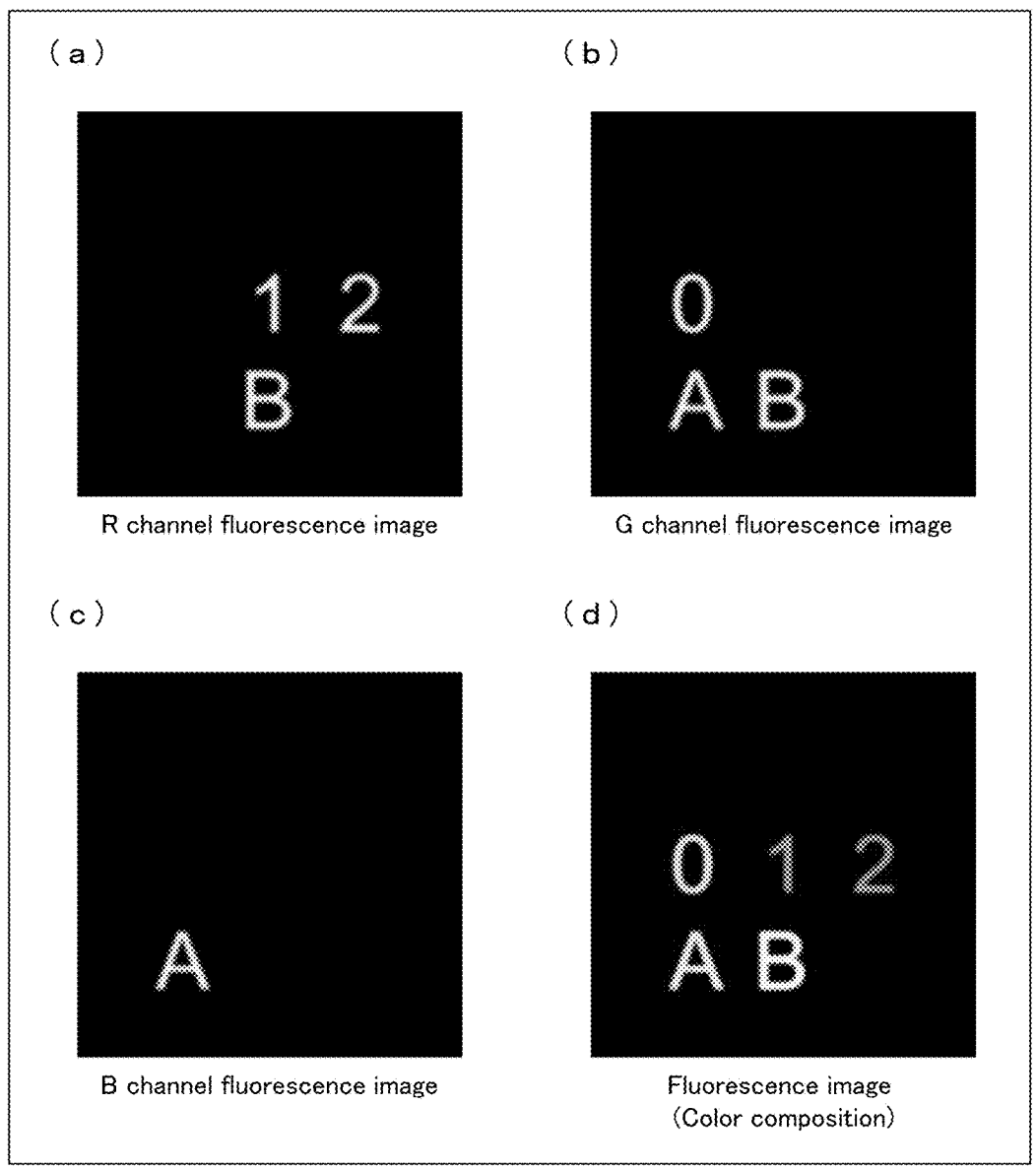

(a) of FIG. 14 shows an R channel image of fluorescence of the subject, (b) of FIG. 14 shows a G channel image of fluorescence of the subject, (c) of FIG. 14 shows a B channel image of fluorescence of the subject, and (d) of FIG. 14 shows a fluorescence image, of the subject, obtained by RGB color composition.

Figure 15:
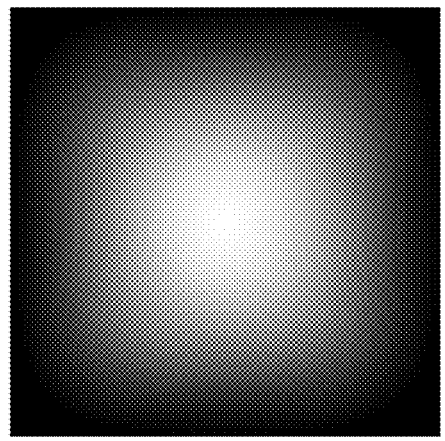

FIG. 15 shows a height distribution of the subject.

Figure 16:

FIG. 16 shows an image of the subject perceived through a normal camera.

Figure 17:
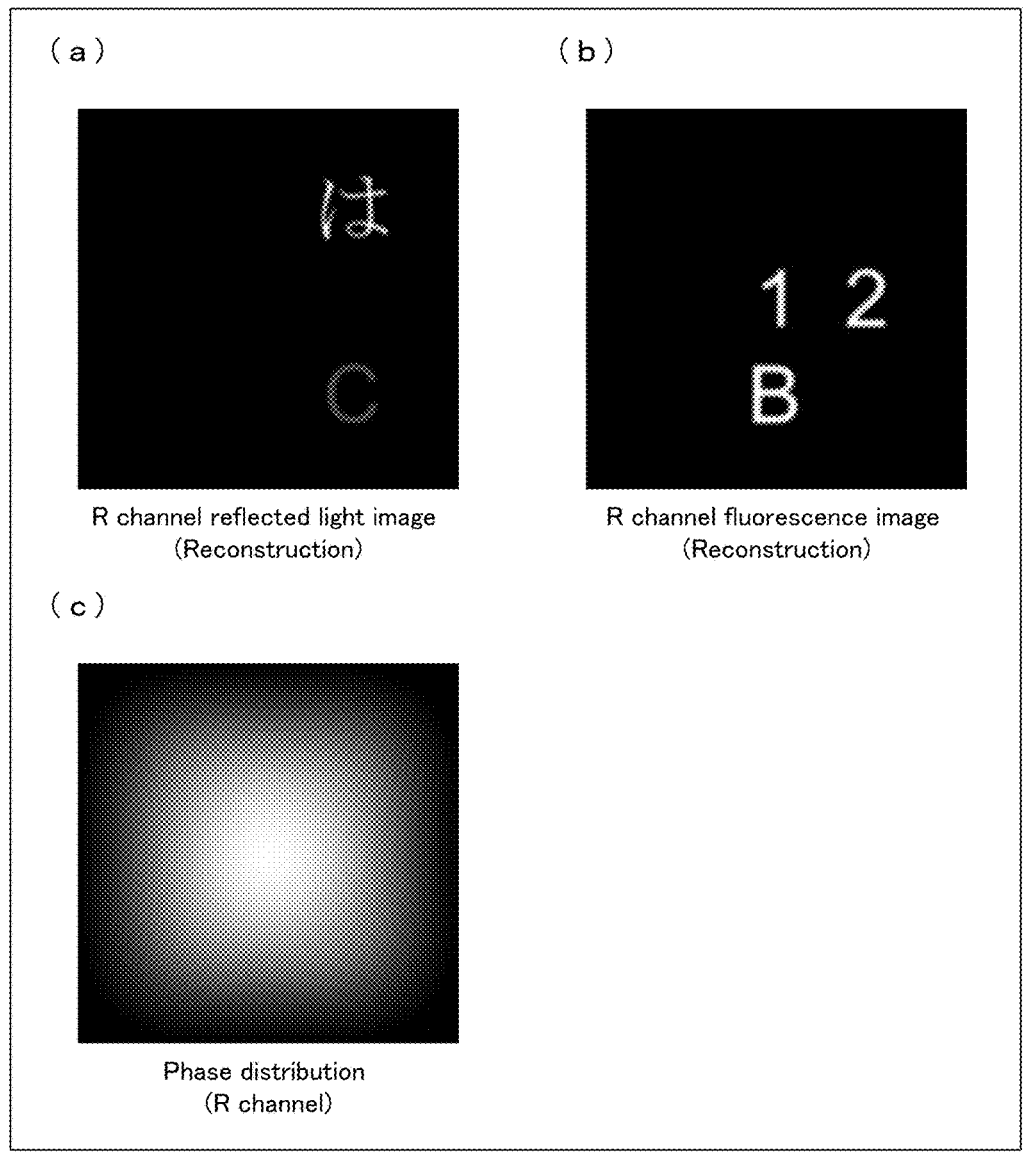

(a), (b), and (c) of FIG. 17 show a reflected light image (reconstructed image), a fluorescence image (reconstructed image), and a phase distribution, respectively, obtained from an R channel recorded image.

Figure 18:
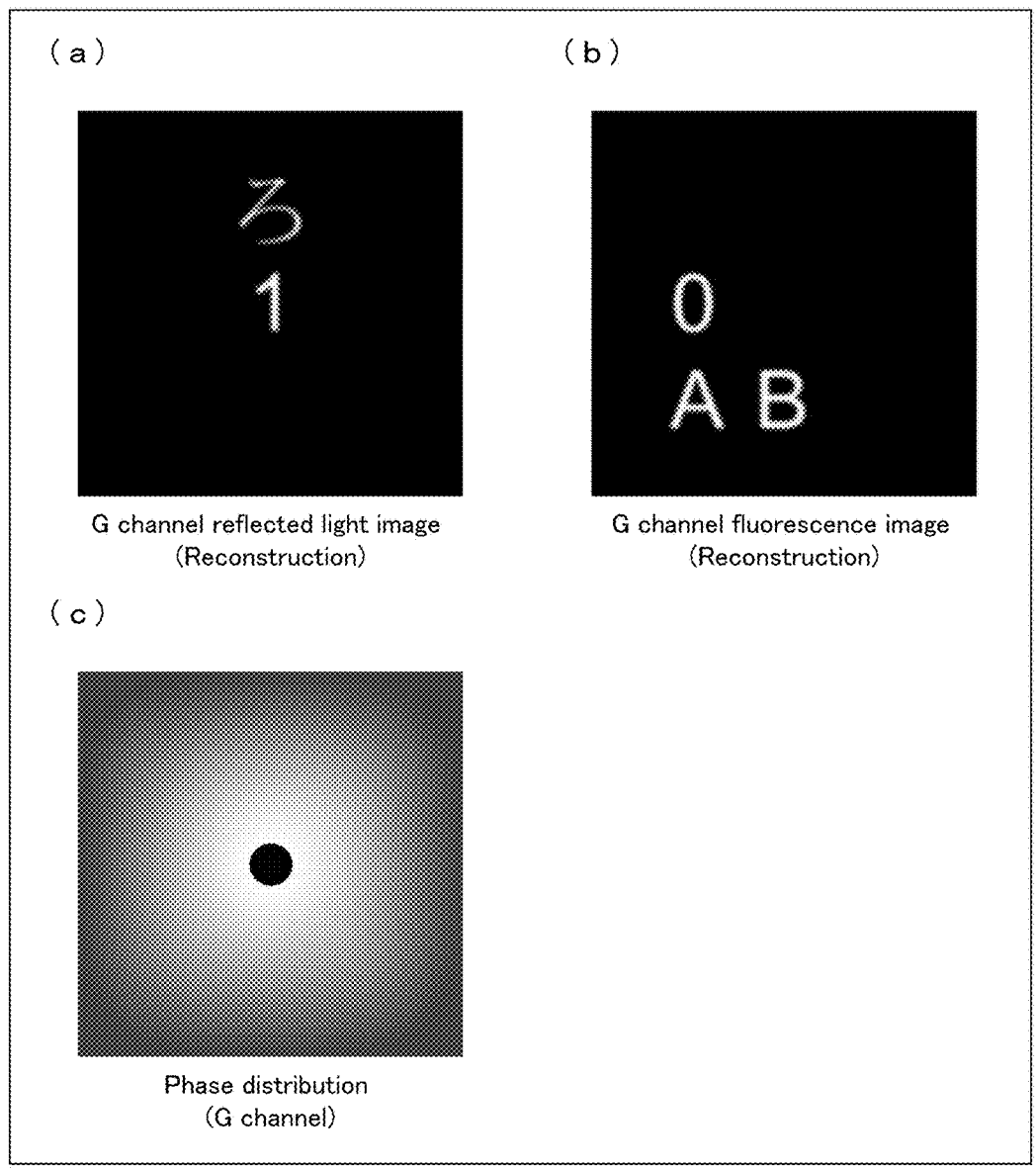

(a), (b), and (c) of FIG. 18 show a reflected light image (reconstructed image), a fluorescence image (reconstructed image), and a phase distribution, respectively, obtained from a G channel recorded image.

Figure 19:
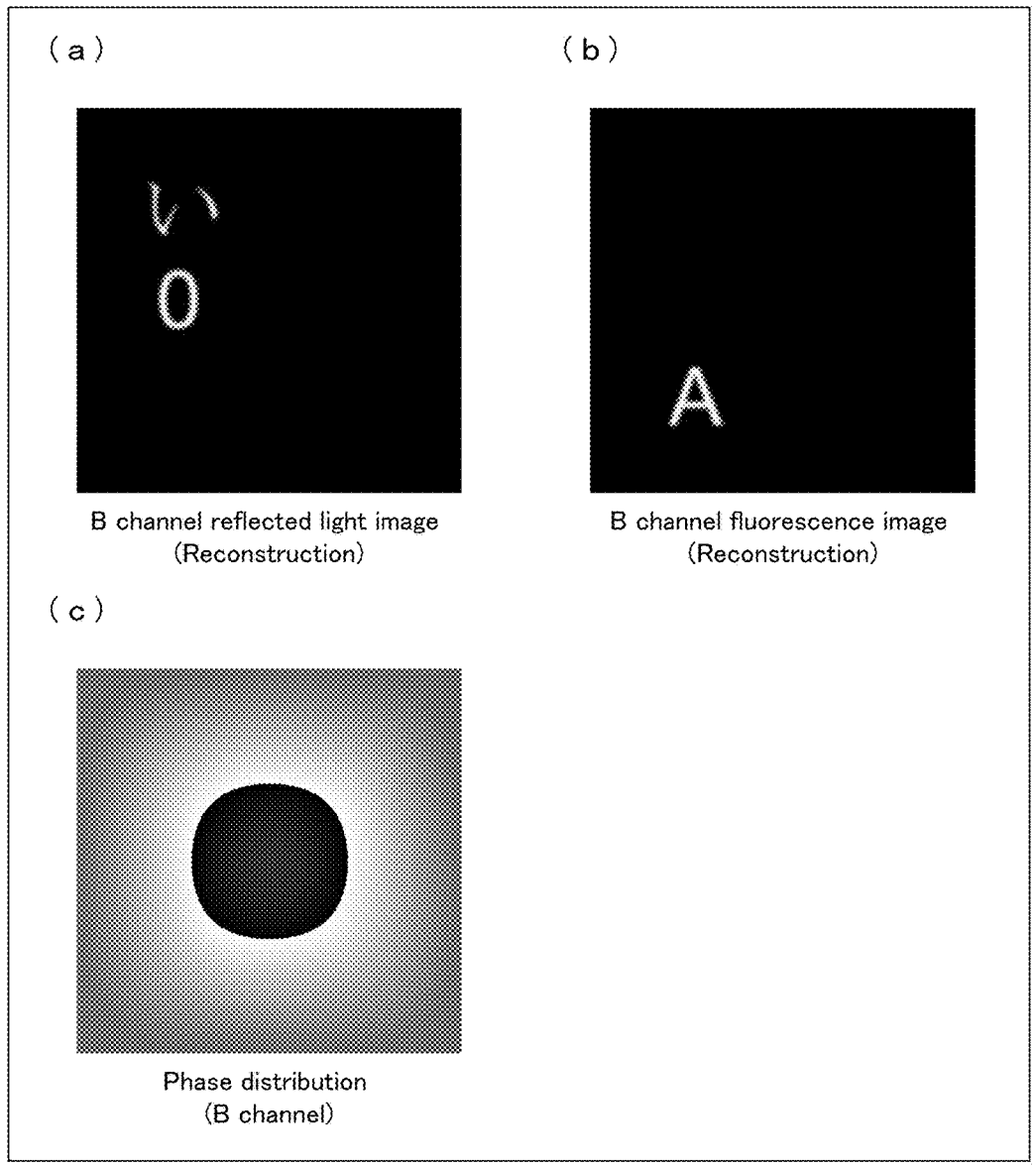

(a), (b), and (c) of FIG. 19 show a reflected light image (reconstructed image), a fluorescence image (reconstructed image), and a phase distribution, respectively, obtained from a B channel recorded image.

Figure 20:
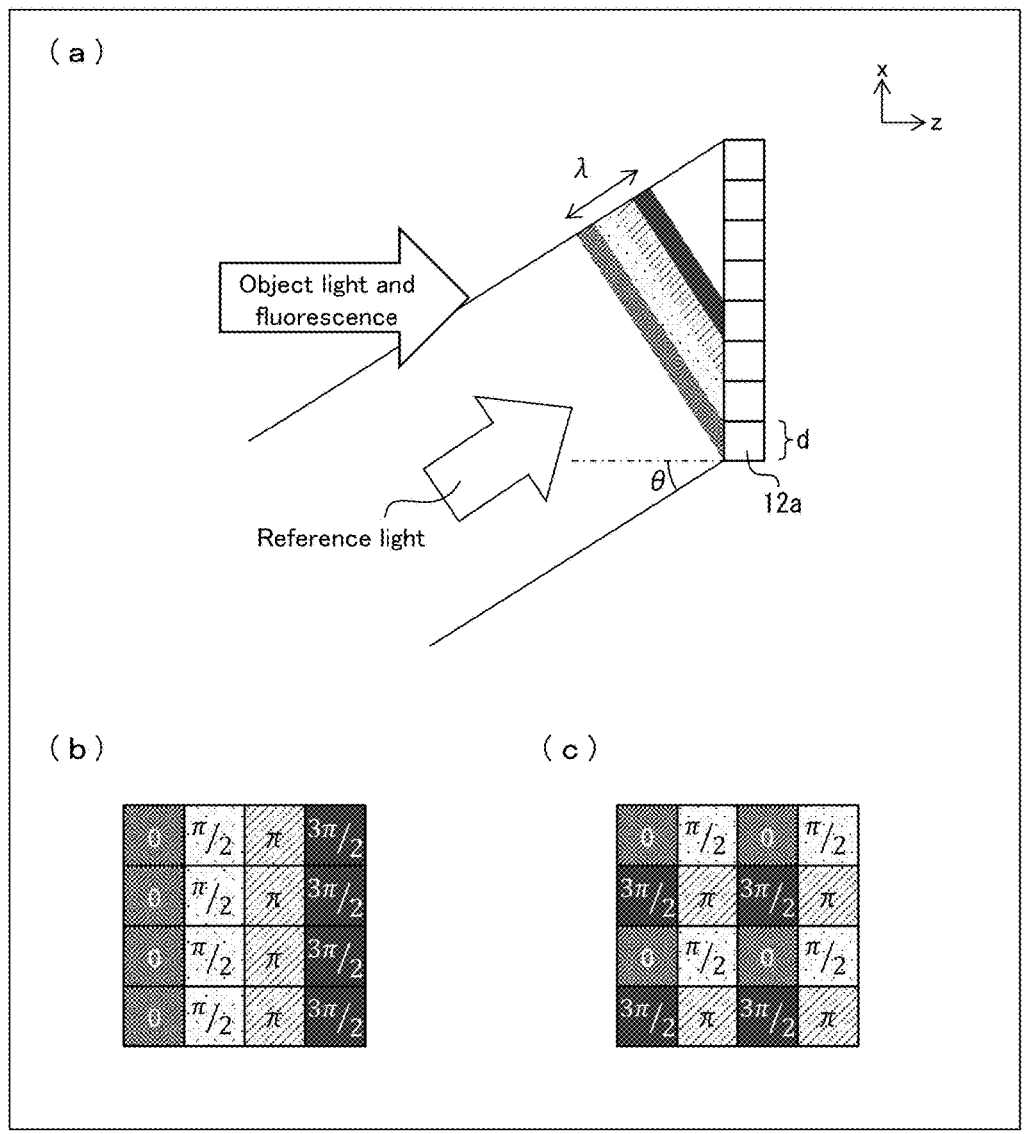

(a) of FIG. 20 is a diagram schematically illustrating a relationship between (i) pixels of an image capturing device and (ii) reference light, and (b) of FIG. 20 is a diagram schematically illustrating phase shift amounts of reference light in part of an image capturing plane in the image capturing device.

Figure 21:
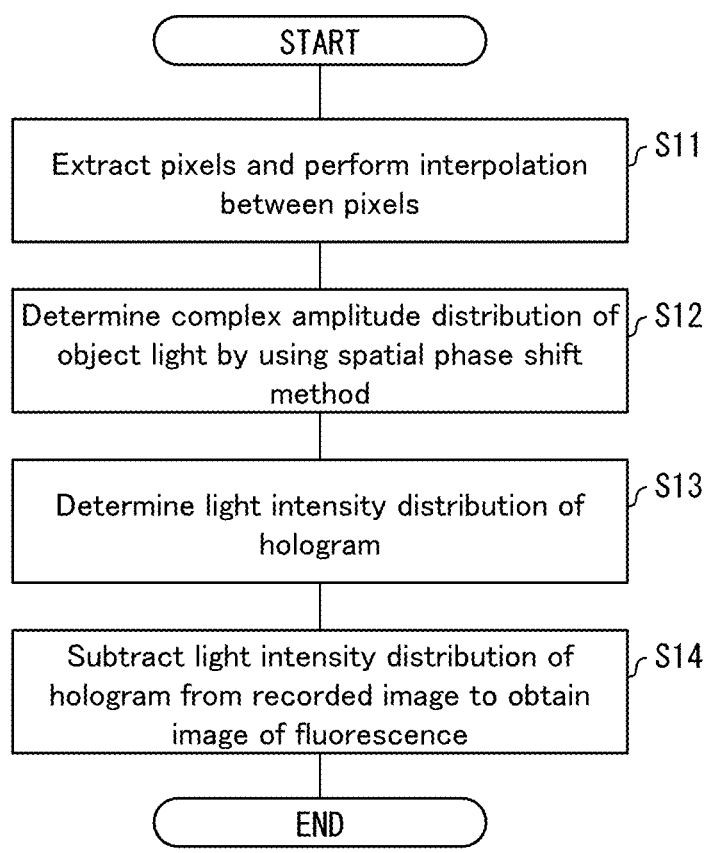

FIG. 21 is a view illustrating a flow of a reconstruction process carried out by a reconstruction device.

Figure 22:
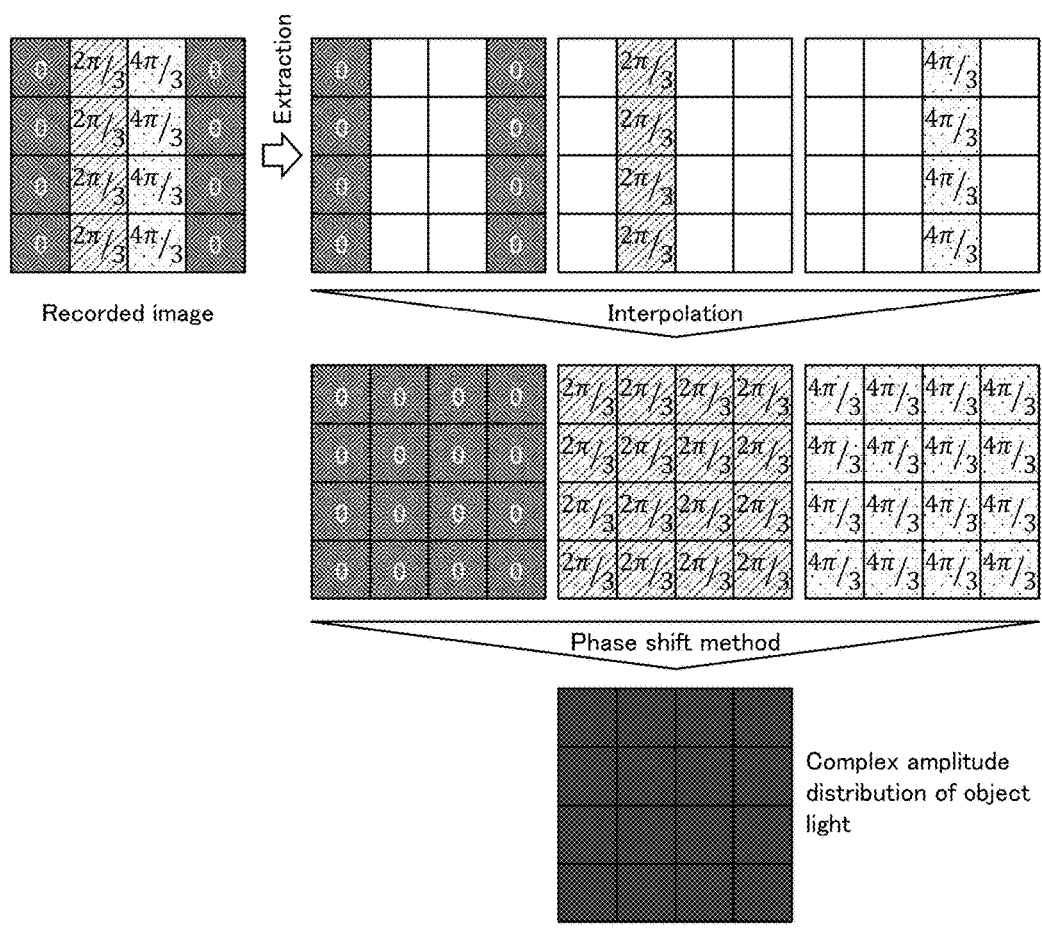

FIG. 22 is a diagram showing an outline of a flow of the reconstruction process.

Figures 23, 24:
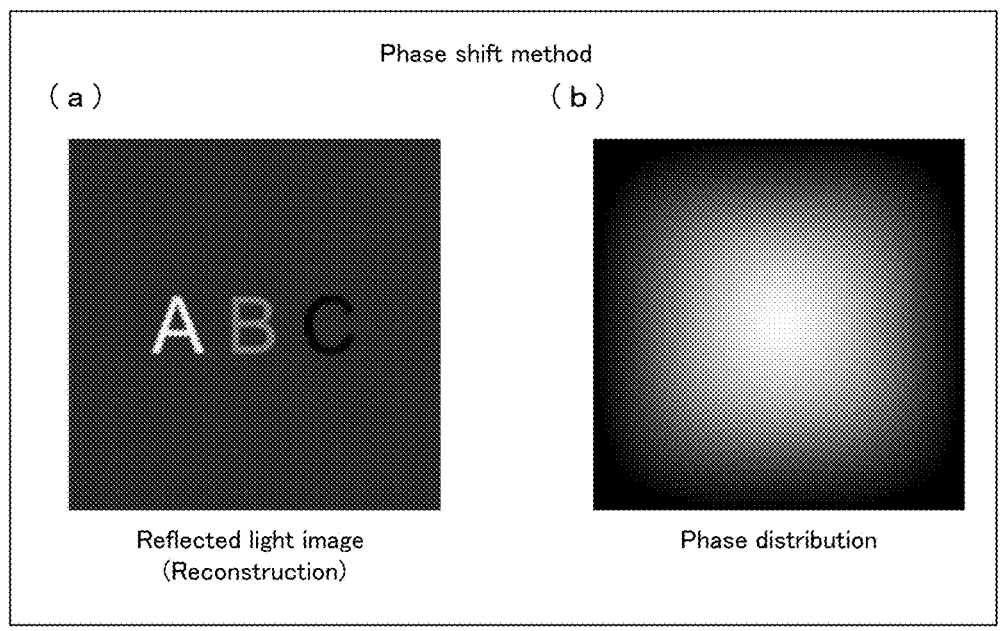

FIG. 23 is a diagram showing phase shift amounts of reference light in an enlarged part of a recorded image.

(a) of FIG. 24 shows a reflected light image (reconstructed image) of a subject which image was obtained by reconstruction using a complex amplitude of object light, and (b) of FIG. 24 shows a phase distribution calculated by using the complex amplitude of the object light.

Figure 25:
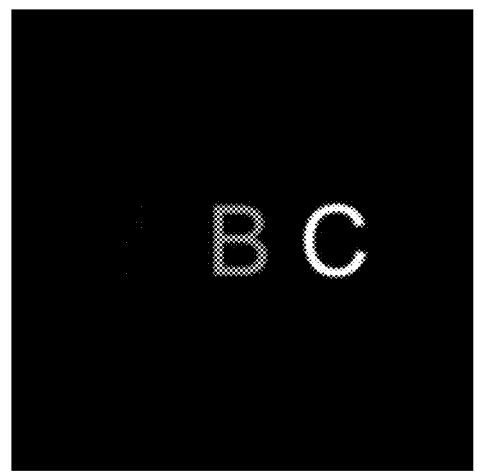

FIG. 25 shows a reconstructed fluorescence image.

DESCRIPTION OF EMBODIMENTS

The following will describe embodiments of the present invention with reference to the drawings. In each of the sections, for convenience of explanation, members having the same functions as those described in the preceding section(s) are given the same reference signs, and as such, are omitted from the description as needed.

Embodiment 1

Embodiment 1 relates to a digital holography apparatus which simultaneously records information of object light and information of fluorescence by a single-shot light exposure. Then, the digital holography apparatus can reconstruct the information of the object light and the information of the fluorescence, by use of the hologram thus recorded, such that these pieces of information are separated from each other.

(Configuration of Digital Holography Apparatus 1)

Figure 1:
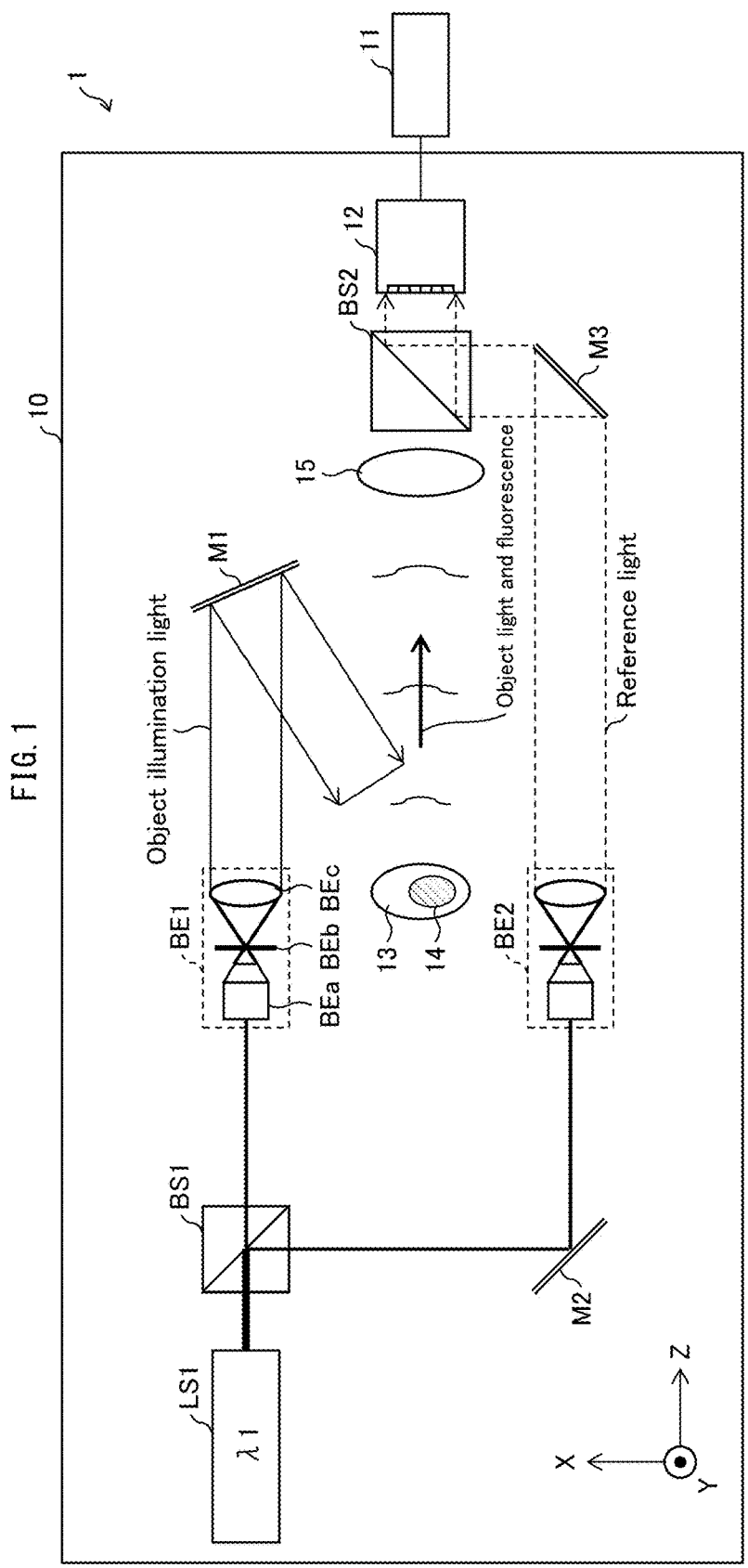
FIG. 1 is a diagram schematically illustrating the configuration of a digital holography apparatus in accordance with an embodiment of the present invention.

FIG. 1 is a diagram schematically illustrating the configuration of a digital holography apparatus 1 in Embodiment 1. The digital holography apparatus 1 is an off-axis type digital holography apparatus. The digital holography apparatus 1 includes a recording device 10 (digital holography recording device) and a reconstruction device 11 (digital holography reconstruction device). The recording device 10 includes an image capturing device 12, a laser light source LS1 (first light source) whose wavelength is $\lambda 1$, and an optical system. The reconstruction device 11 can be constituted by a calculator such as a computer. Note that not only visible light but also invisible light (infrared rays, ultraviolet rays, X rays, etc.) can be used as laser light.

The optical system, which is provided with a plurality of optical elements such as a mirror, guides laser light (coherent light) having a wavelength $\lambda 1$ (hereinafter referred to simply as "$\lambda 1$ laser light") to a subject 13 (object) and the image capturing device 12. Specifically, the optical system includes, as the plurality of optical elements, beam splitters BS1 and BS2, mirrors M1 to M3, beam expanders BE1 and BE2, and an image forming element 15 (image-forming optical element). The beam expanders BE1 and BE2 each include an objective lens BEa, a pinhole BEb, and a collimator lens BEc. The beam splitters BS1 and BS2 are each constituted by a semitransparent mirror. The image forming element 15 includes a lens. However, this is not the only structure of the image forming element 15. Alternatively, the image forming element 15 can be any optical element for forming an image.

The image capturing device 12, which has an image capturing plane in which a plurality of pixels for capturing an image are arranged in an x direction and in a y direction, records the intensity of light that reaches the image capturing plane. The x direction is vertical to the y direction. A z direction is vertical to the x direction and the y direction. The image capturing device 12 has an image capturing element such as a CCD or a CMOS. The image capturing device 12 records interference fringes formed on the image capturing plane. The interference fringes are a hologram having information of object light. Note that each of the pixels has a limited light receiving region. Thus, light intensity detected by each of the pixels is an integral of light intensity of interference fringes in the light receiving region. Since the image capturing device 12 has no color filter, each of the pixels of the image capturing device 12 can receive light beams of different wavelengths at once. That is, the image capturing device 12 is a monochromatic image capturing device. The image capturing device 12 outputs, to the reconstruction device 11, image data that represents a captured image. Details of the reconstruction device 11 will be described later.

(Object Light, Reference Light, and Fluorescence)

The $\lambda 1$ laser light having been emitted from the laser light source LS1 is split by the beam splitter BS1 into reference light and object illumination light.

The object illumination light having the wavelength $\lambda 1$ (hereinafter referred to simply as "$\lambda 1$ object illumination light"), which is one part of the $\lambda 1$ laser light split by the beam splitter BS1, passes through the mirror M1 and is then directed onto the subject 13. The object illumination light is scattered by the subject 13 (reflected by the subject 13 or passes through the subject 13) or diffracted by the subject 13 to turn into object light. In this embodiment, the object light is reflected light from the subject 13. Alternatively, the object light can be transmitted light which passes through the subject 13 when the subject 13 is irradiated with the object illumination light from its back. The object light generated by irradiation of the subject 13 with the object illumination light passes through the image forming element 15 and the beam splitter BS2 and then enters the image capturing plane of the image capturing device 12.

In this embodiment, the subject 13 includes a fluorescent material 14. The λ1 object illumination light also functions to excite the fluorescent material 14. The fluorescent material 14 excited by the λ1 object illumination light emits fluorescence of a given wavelength determined by a fluorescent molecule. The wavelength λ1 is shorter than a wavelength of fluorescence. However, in a case where two-photon excitation or multi-photon excitation is employed, the wavelength λ1 can be equal to or longer than the wavelength of fluorescence. Similarly to the object light, the fluorescence having been emitted from the fluorescent material 14 passes through the image forming element 15 and the beam splitter BS2 and then enters the image capturing plane of the image capturing device 12.

The reference light having the wavelength λ1 (hereinafter referred to simply as "λ1 reference light"), which is the other part of the λ1 laser light split by the beam splitter BS1, goes through the mirror M2, the beam expander BE2, and the mirror M3, is reflected by the beam splitter BS2, and then enters the image capturing plane of the image capturing device 12. Individual angles at which the object light and the reference light enter the image capturing plane can be adjusted by use of the optical element(s) (e.g., a beam splitter and a mirror) included in the optical system.

In this embodiment, the object light from the center of the subject 13 is assumed to enter the center of the image capturing plane of the image capturing device 12 at an angle perpendicular to the center of the image capturing plane of the image capturing device 12. In other words, the center of the subject 13 is located on a line passing through the center of the image capturing plane and being perpendicular to the image capturing plane. On the other hand, the reference light enters the image capturing plane obliquely. That is, there is an angle difference between an optical axis of the object light incident on the image capturing plane and an optical axis of the reference light incident on the image capturing plane.

The object light and the fluorescence are focused on the image capturing plane of the image capturing device 12 by the image forming element 15 so as to form an image on the image capturing plane of the image capturing device 12. The object light interferes with the reference light to form a hologram (image-forming type hologram) on the image capturing plane. Meanwhile, the fluorescence, which has low coherency, is called incoherent light. Further, the fluorescence is different in wavelength from the object light and the reference light. Thus, the fluorescence does not interfere with the object light or the reference light. The image capturing device 12 captures a superimposed image in which the hologram and an image of the focused fluorescence are superimposed. Note that, for example, an optical filter for decaying light of a wavelength equivalent to the wavelength of the laser light and passing through light of a wavelength equivalent to the wavelength of the fluorescence can be provided upstream from the image capturing plane. In a case where the intensity of the fluorescence emitted from the fluorescent material 14 is extremely lower than that of the object light, it is possible to use the optical filter to decrease (i) the intensity of the object light or the reference light or (ii) the respective intensities of both the object light and the reference light, in order to prevent the image of the fluorescence from being buried in the hologram.

(Configuration of Reconstruction Device 11)

Figure 2:
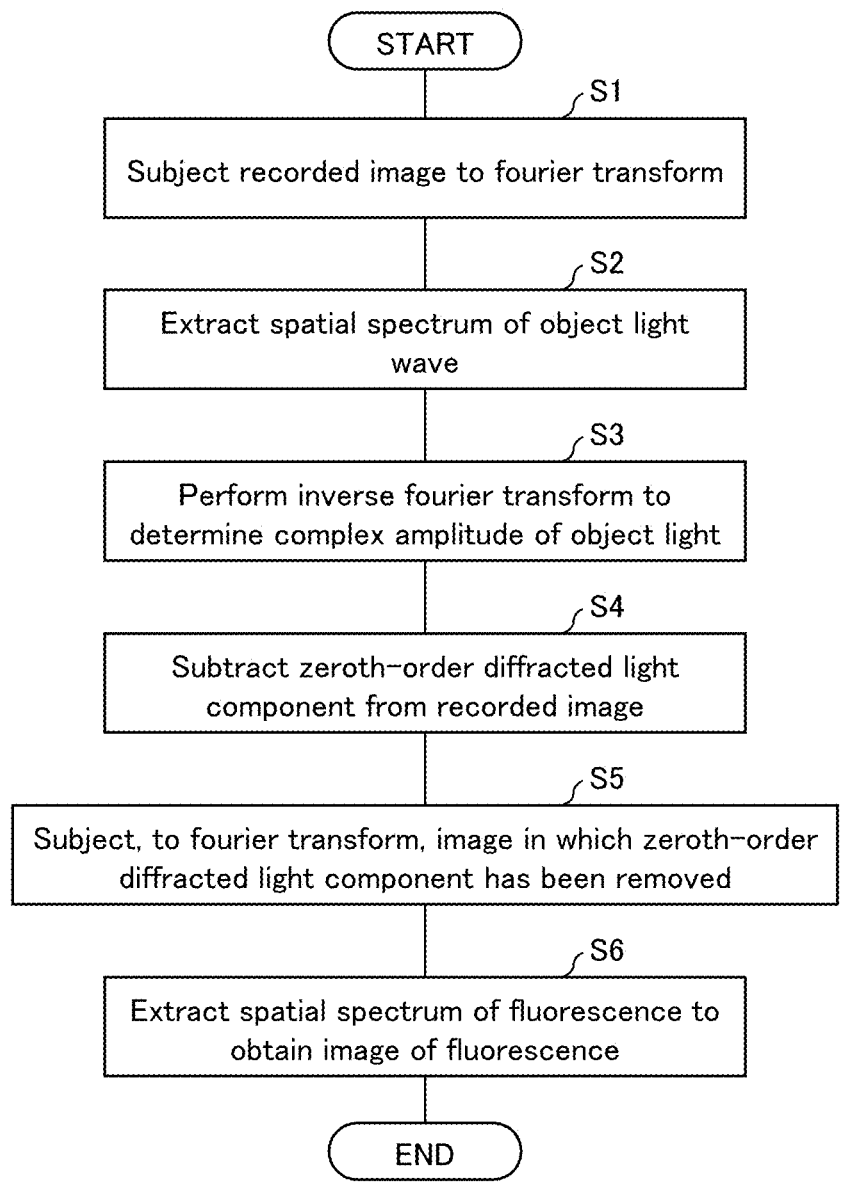
FIG. 2 is a view illustrating a flow of a reconstruction process carried out by a reconstruction device in accordance with an embodiment of the present invention.

FIG. 2 is a view illustrating a flow of a reconstruction process carried out by the reconstruction device 11 of Embodiment 1. The reconstruction device 11 carries out reconstruction of the image of the subject 13 and reconstruction of the image of the fluorescence, by using the image (containing a hologram and fluorescence) recorded by the image capturing device 12. The recorded image, which is a superimposed image in which (i) the hologram containing information of the object light (i.e., three-dimensional shape information of the subject 13) and (ii) the fluorescence are superimposed, cannot be directly used for the reconstruction in a publicly known digital holography technique.

In this embodiment, a value of each pixel of the recorded image is a sum of light intensity Ih of the hologram and light intensity If of the fluorescence. The light intensities Ih and If vary from pixel to pixel. Since the fluorescence is focused on the image capturing plane, the light intensity If of the fluorescence represents a distribution of fluorescence as viewed from the image capturing device 12. The light intensity Ih of the hologram is expressed as follows:

$$Ih=|O|^2+|R|^2 2|O||R|\cos \varphi \qquad (1)$$

wherein |O| is an amplitude of the object light, |R| is an amplitude of the reference light, $|O|^2$ is an intensity of the object light, $|R|^2$ is an intensity of the reference light, and φ is a phase difference of the object light relative to the reference light. |O|, |R|, and φ can vary from pixel to pixel. Note that since the reference light is a plane wave expanded from laser light, it is possible to assume (presume) that a value of the intensity of the reference light is a uniform value or a value having a predetermined distribution (e.g., Gaussian distribution). Note that in order to reconstruct the images with a higher degree of accuracy, it is possible to measure intensity distribution of only the reference light before or after the recording. Measurement of the intensity distribution of the reference light corresponds to a calibration for increasing the accuracy of reconstruction. Thus, $|R|^2$ can be dealt with as a known value.

Specifically, the reconstruction device 11 subjects the recorded image to two-dimensional Fourier transform (S1). The hologram contains interference fringes formed, with various spacings therebetween, by interference between the reference light and the object light. When the image containing this hologram is subjected to Fourier transform, individual spectrums of an object light wave (first-order diffracted light), zeroth-order diffracted light, and a conjugate image (minus first-order diffracted light) appear in accordance with the spacings between the fringes. Hereinafter, a plane and spectrum obtained after the two-dimensional Fourier transform are referred to as "spatial frequency plane" and "spatial spectrum", respectively.

Figure 3:
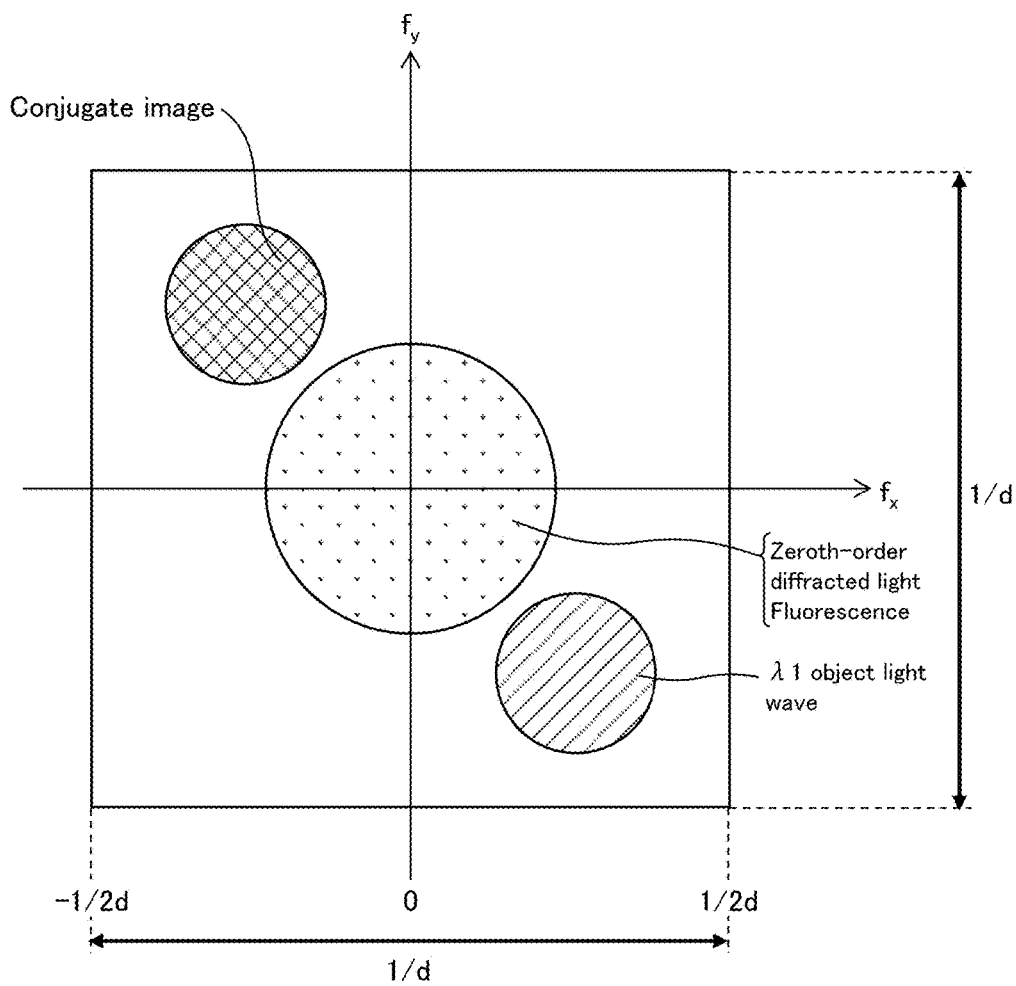
FIG. 3 is a view schematically illustrating an image obtained by subjecting a recorded image to two-dimensional Fourier transform.

FIG. 3 is a view schematically illustrating an image obtained by subjecting a recorded image to two-dimensional Fourier transform. In FIG. 3, a lateral axis represents a spatial frequency fx on an x axis, while a longitudinal axis represents a spatial frequency fy on a y axis. In a spatial frequency plane of an image containing (i) a hologram and an image of fluorescence, there exist a spatial spectrum of zeroth-order diffracted light with the wavelength λ1, a spatial spectrum of an object light wave (first-order diffracted light) with the wavelength λ1, a spatial spectrum of a conjugate image (minus first-order diffracted light) with the wavelength λ1, and a spatial spectrum of fluorescence. Note that the spatial spectrum of the conjugate image appears at a position symmetric about the origin point to the spatial spectrum of the object light wave. Note that in this embodiment, each spatial spectrum is circular. Such a spatial spectrum is obtained, for example, when a light transmission filter (opening or aperture) with a shape similar to the shape of each spatial spectrum is placed on the path of object light. A spatial frequency range which is covered for recording by the image capturing device is a 1/d-wide region (where d is a spacing between pixels) centered around the origin point in the spatial frequency plane.

The spatial spectrum of the zeroth-order diffracted light is distributed around the origin point. Also, the spatial spectrum of the fluorescence is often distributed around the origin point. Thus, the spatial spectrum of the zeroth-order diffracted light and the spatial spectrum of the fluorescence are distributed so as to at least partially overlap each other in the spatial frequency plane. Note that in a case where the recording device 10 is configured such that an opening or an aperture is placed between the subject 13 and the image capturing device 12 (for example, near the image forming element 15), a high frequency component in the spatial spectrum of the fluorescence can be cut. This allows the spatial spectrum of the fluorescence to be located mainly in a low frequency region (near the origin point).

On the other hand, the spatial spectrum of the object light wave with λ1 appears closer to a high frequency end than the spatial spectrum of the zeroth-order diffracted light. In the recording device 10, an increase in angle difference between the optical axis of the object light incident on the image capturing plane and the optical axis of the reference light incident on the image capturing plane decreases a fringe spacing between the interference fringes. This shifts the spatial spectrum of the object light wave to the high frequency end. By providing some angle difference between the optical axis of the object light and the optical axis of the reference light, it is possible to prevent an overlap between the spatial spectrum of the object light wave and the spatial spectrum of the zeroth-order diffracted light in the spatial frequency plane.

The reconstruction device 11 extracts the spatial spectrum of the object light wave from the Fourier-transformed image (S2). For example, the reconstruction device 11 extracts, as the spatial spectrum of the object light wave, a predetermined range of the Fourier-transformed image. A range of distribution of the spatial spectrum of the object light wave depends on a wavelength of the object light, incidence angles of the object light and the reference light, and an angle of visibility of the subject 13 (which angle can be limited by the opening or the aperture) as viewed from the image capturing device 12. Thus, the range of distribution of the spatial spectrum of the object light wave can be known in advance.

The reconstruction device 11 subjects the extracted spatial spectrum of the object light wave to inverse Fourier transform. Further, the reconstruction device 11 corrects the amount of phase modulation which is determined by a tilt angle of the reference light. Based on the results of the inverse Fourier transform and the correction of the amount of phase modulation, the reconstruction device 11 obtains a complex amplitude of the object light (|O| and a phase corrected by the amount of phase modulation for the reference light from φ) for each pixel (S3). The reconstruction device 11 can reconstruct the image of the subject 13 based on the obtained complex amplitude of the object light.

Note that the result obtained by the inverse Fourier transform represents the one in which the zeroth-order diffracted light, the conjugate image, and the fluorescence are removed from the recorded image (containing the hologram and the fluorescence). The phase of the reference light varies from pixel to pixel (In a case where the reference light is a plane wave, the phase of the reference light changes periodically.). As used herein, the expression "correcting the amount of phase modulation" means correcting (cancelling), according to a phase distribution of the reference light, the amount of phase modulation (determined according to a phase of the reference light) contained in φ, of the object light, obtained from the result of the inverse Fourier transform.

The reconstruction device 11 obtains $|O|^2$ for each pixel from the complex amplitude of the object light (S4). As described earlier, the intensity $|R|^2$ of the reference light is known. The reconstruction device 11 obtains a zeroth-order diffracted light component $(|O|^2+|R|^2)$ from the complex amplitude of the object light. With all the known values on the right side of the expression (1), the reconstruction device 11 can determine the light intensity Ih of the hologram.

The reconstruction device 11 subtracts the zeroth-order diffracted light component $(|O|^2+|R|^2)$ from a pixel value of the recorded image. The reconstruction device 11 subjects, to Fourier transform, a resulting image in which the zeroth-order diffracted light component has been removed (S5).

In the spatial frequency plane, the spatial spectrum of the object light wave and the spatial spectrum of the fluorescence are separated. In the spatial frequency plane, the zeroth-order diffracted light component which overlaps the fluorescence has been removed. Thus, the reconstruction device 11 can extract the spatial spectrum of the fluorescence by extracting a predetermined area centered around the origin point from the Fourier-transformed image in which the zeroth-order diffracted light component has been removed. The reconstruction device 11 subjects the extracted spatial spectrum of the fluorescence to inverse Fourier transform to obtain an intensity distribution of the fluorescence (image of the fluorescence) (S6). Note that the zeroth-order diffracted light component can be subtracted from the recorded image as described earlier, or alternatively, a Fourier-transformed zeroth-order diffracted light component can be subtracted from the Fourier-transformed image. The zeroth-order diffracted light component can be removed either in a real space or in a Fourier space.

In a manner as described above, the reconstruction device 11 can separately reconstruct the image of the fluorescence based on the superimposed image in which the hologram and the image of the fluorescence are superimposed. Further, the reconstruction device 11 can reconstruct the image of the subject 13 based on the complex amplitude of the object light to obtain three-dimensional shape information of the subject 13. Note that a publicly known technique can be employed as a method for reconstructing an image based on the extracted spatial spectrum of the object light wave.

In Embodiment 1, the recording device 10 generates the object light and excites the fluorescent material 14 through the use of the object illumination light emitted from a single laser light source LS1. This eliminates the need for another light source only for exciting the fluorescent material 14 and thus achieves downsizing of the recording device 10.

Further, the recording device 10 simultaneously captures a hologram and an image of the fluorescence, while tilting an optical axis of reference light with respect to an optical axis of the object light, so that the object light and the fluorescence can be reconstructed separately. That is, the recording device 10 carries out image capture so that, in the spatial frequency plane, the spatial spectrum of the object light wave is separated from the spatial spectrum of the zeroth-order diffracted light and the spatial spectrum of the fluorescence. From the hologram recorded in such a manner, the reconstruction device 11 separately reconstructs the object light and the fluorescence as described earlier. The digital holography apparatus 1 captures, as a single image, the hologram and the fluorescence simultaneously and thus enables recording of a moving picture at a frame rate of the image capturing device 12. Further, the optical system of the recording device 10 can be a transmission type optical system in place of a reflection type optical system and can record light which includes transmitted light, diffracted light, or scattered light, in place of reflection light. The digital holography apparatus 1 can be used for, for example, analysis of movement of a target in a cell, high-speed characteristic evaluation of a transparent material such as a fluorite and a paint, and high-speed characteristic evaluation of a rough-surface product or a scatterer such as fish, a plant, and a fruit.

Note that a color image capturing device can be used as the image capturing device 12. The color image capturing device records respective images of colors of R, G, and B (red, green, and blue). In this case, unless the wavelength of the object light and the wavelength of the fluorescence are far apart, each color image can contain a hologram and an image of the fluorescence in a superimposed manner. Further, since the light source produces a plurality of light beams of different wavelengths, fluorescence produced can have a wavelength which is the same as any of the wavelengths of the light beams from the light source. Thus, for example, the reconstruction device 11 carries out, for each of the images of colors of R, G, B, separation and reconstruction of the object light and the fluorescence. For example, for the fluorescence, three reconstructed images corresponding to R, G, and B, are obtained. Accordingly, even in a case where the fluorescent material 14 contained in the subject 13 is not known, it is possible to determine the color of the fluorescence. Therefore, a digital holography apparatus using a color image capturing device can be utilized in, for example, wavelength spectrum simultaneous analysis for reflected light and fluorescence of a substance. Note that, for example, in a case where the object illumination light is infrared rays, the fluorescence is visible light having a wavelength longer than a wavelength of the object illumination light. In this case, for example, an infrared image capturing device can be used. In an alternative example, an image capturing device, like a color image capturing device, with different wavelength selection filters for different pixels (individual filters that selectively transmit light beams of different wavelengths in the invisible light range) can be used to image object light which is invisible light, reference light, and fluorescence.

Thus, the recording device 10 records (captures) a superimposed image in which (i) a hologram formed by coherent light and (ii) an image of a subject which image is formed by incoherent light emitted by the subject are superimposed. The reconstruction device 11 separately reconstructs, based on the recorded (captured) image, the image of the subject which image is formed by incoherent light. In this embodiment, an example case in which the incoherent light emitted by the subject is fluorescence has been described. Needless to say, the incoherent light emitted by the subject is not limited to fluorescence and can be any incoherent light (e.g., phosphorescence or light emitted by electric discharge). This also applies to other embodiments.

Note that after the step S3 in the flow shown in FIG. 2, the reconstruction device 11 can determine the light intensity Ih of the hologram based on the determined complex amplitude of the object light. This allows the reconstruction device 11 to subtract the light intensity Ih of the hologram from the recorded image to thereby extract only the image of the fluorescence. In this case, the reconstruction device 11 can omit the second Fourier transform process (S5) and the inverse Fourier transform process (S6). The Fourier transform process is a computationally intensive process. Therefore, by performing the processing as described above, the reconstruction device 11 can perform the process of reconstructing the image of the fluorescence at a high speed.

However, in order to accurately calculate the light intensity Ih of the hologram, it is necessary to accurately determine the phase of the reference light for each pixel and then input the phase to the reconstruction device 11. A user can determine the phase of the reference light by any one of the following approaches: (1) measuring the angle of the optical axis of the reference light with respect to the optical axis of the object light in the optical system; (2) in the Fourier-transformed image based on the recorded image, calculating the angle of the optical axis of the reference light based on (i) the distance from the origin point to the center of the spatial spectrum of the object light wave and (ii) the wavelength; and (3) estimating (assuming) the angle of the optical axis of the reference light. In the approach (1), it is also a possible way to previously obtain information of the angle difference by performing the calibration process before or after the measurement (recording of hologram and fluorescence). In the calibration process, a hologram is recorded in advance in a state in which a mirror or a reference object is placed in the object light path in order to measure the angle of the optical axis or in a state in which a plane wave or a spherical wave that propagates in the direction along the optical axis is set as the object light. Then, the recorded hologram is subjected to Fourier transform, and the spatial spectrum of the object light is extracted from the Fourier-transformed hologram to obtain phase information of the object light. In a case where light having an uncomplicated phase distribution, such as a plane wave, is used, information on the phase modulation amount based on the reference light is easily extracted. This consequently enables measurement (calculation) of the angle difference with a higher degree of accuracy. If the measurement or estimation is not accurate, then the light intensity of a hologram would be calculated with a low degree of accuracy. This consequently decreases the accuracy of a resulting image of the fluorescence. On the other hand, the intensity of zeroth-order diffracted light can be obtained regardless of the phase of the reference light. Therefore, performing the processing as in the flow shown in FIG. 2 enables the accuracy of the resulting image of the fluorescence to be increased. Further, the reconstruction method in Embodiment 1 achieves a higher degree of accuracy of the image of the fluorescence than the reconstruction method in Embodiment 4 (described later).

Further, the recording device 10 can carry out image capture in a state in which object light, reference light, and fluorescence are not generated (blocked), so that an image for calibration is outputted to the reconstruction device 11. This image is a captured image of stray light as noise. The reconstruction device 11 can be configured such that an image obtained by subtracting a pixel value of an image of stray light from a pixel value (intensity) of a recorded image is used as a calibrated recorded image. This eliminates the influence of noise such as stray light and thus enables an increase in reconstruction accuracy.

Embodiment 2

Embodiment 2 will describe a case where a plurality of laser light sources having different wavelengths are used.

(Recording of Object Light and Fluorescence)

Figure 4:
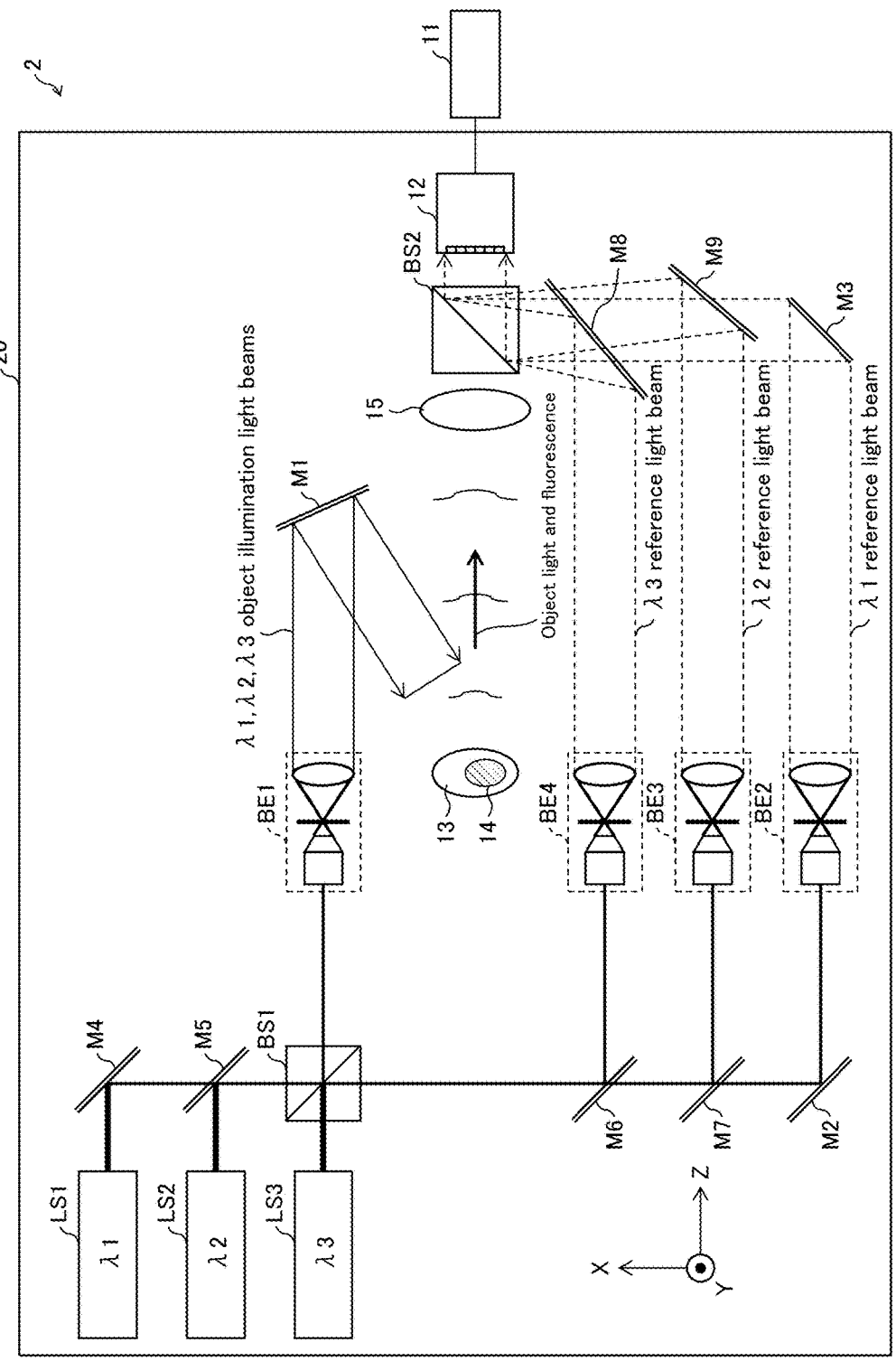
FIG. 4 is a diagram schematically illustrating the configuration of a digital holography apparatus in accordance with another embodiment of the present invention.

FIG. 4 is a diagram schematically illustrating the configuration of a digital holography apparatus 2 in Embodiment 2. The digital holography apparatus 2 is an off-axis type digital holography apparatus. The digital holography apparatus 2 includes a recording device 20 (digital holography recording device) and a reconstruction device 11. The recording device 20 includes an image capturing device 12, a laser light source LS1 whose wavelength is $\lambda 1$, a laser light source LS2 (first light source) whose wavelength is $\lambda 2$, a laser light source LS3 (second light source) whose wavelength is $\lambda 3$, and an optical system.

The optical system, which is provided with a plurality of optical elements such as a mirror, guides laser light (coherent light) having a wavelength $\lambda 1$, laser light (coherent light) having a wavelength $\lambda 2$, and laser light (coherent light) having a wavelength $\lambda 3$ (hereinafter referred to simply as "$\lambda 1$ laser light", "$\lambda 2$ laser light", and "$\lambda 3$ laser light", respectively) to a subject 13 and the image capturing device 12. Specifically, the optical system includes, as the plurality of optical elements, beam splitters BS1 and BS2, mirrors M1 to M9, beam expanders BE1 to BE4, and an image forming element 15. The mirrors M5 to M9 can be each constituted by a dichroic mirror or a polarization beam splitter.

The $\lambda 1$ laser light, $\lambda 2$ laser light, and $\lambda 3$ laser light are aligned coaxially by the mirror M4, the mirror M5, and the beam splitter BS1. The $\lambda 1$ laser light, the $\lambda 2$ laser light, and the $\lambda 3$ laser light are each split into an object illumination light beam and a reference light beam by the beam splitter BS1.

An object illumination light beam having the wavelength $\lambda 1$, an object illumination light beam having a wavelength $\lambda 2$, and an object illumination light beam having a wavelength $\lambda 3$ (hereinafter referred to simply as "$\lambda 1$ object illumination light beam", "$\lambda 2$ object illumination light beam", and "$\lambda 3$ object illumination light beam", respectively) are directed onto the subject 13. An object light beam having the wavelength $\lambda 1$, an object light beam having the wavelength $\lambda 2$, and an object light beam having the wavelength $\lambda 3$, which have been outputted from the subject 13, pass through the image forming element 15 and the beam splitter BS2, and enter the image capturing plane of the image capturing device 12.

The $\lambda 2$ object illumination light beam and the $\lambda 3$ object illumination light beam also function to excite the fluorescent material 14 (function as excitation light). In addition, the fluorescent material 14 can be excited by the $\lambda 1$ object illumination light beam. The fluorescent material 14 is excited by a plurality of object illumination light beams. This enhances the intensity of fluorescence emitted from the fluorescent material 14. Similarly to the object light beams, the fluorescence having been emitted from the fluorescent material 14 passes through the image forming element 15 and the beam splitter BS2 and then enters the image capturing plane of the image capturing device 12.

A reference light beam having the wavelength $\lambda 1$ (hereinafter referred to simply as "$\lambda 1$ reference light beam") passes through the mirrors M6 and M7, goes through the mirror M2, the beam expander BE2, and the mirror M3, passes through the mirrors M9 and M8. Subsequently, the $\lambda 1$ reference light beam is reflected by the beam splitter BS2 and then enters the image capturing plane of the image capturing device 12.

A reference light having the wavelength $\lambda 2$ (hereinafter referred to simply as "$\lambda 2$ reference light beam") passes through the mirror M6, is reflected by the mirror M7, goes through the beam expander BE3, is reflected by the mirror M9, and passes through the mirror M9. Subsequently, the $\lambda 2$ reference light beam is reflected by the beam splitter BS2 and then enters the image capturing plane of the image capturing device 12.

A reference light beam having the wavelength $\lambda 3$ (hereinafter referred to simply as "$\lambda 3$ reference light beam") is reflected by the mirror M6, goes through the beam expander BE4, and is reflected by the mirror M8. Subsequently, the $\lambda 3$ reference light beam is reflected by the beam splitter BS2 and then enters the image capturing plane of the image capturing device 12.

The recording device 20 includes different paths for the respective wavelengths of the reference light beams to make the reference light beams incident on the image capturing plane at different incidence angles for the individual wavelengths (incidence angle on an x-z plane and incidence angle on a y-z plane).

The image capturing device 12 is a monochromatic image capturing device. The image capturing device 12 captures a superimposed image in which (i) a plurality of holograms corresponding to a plurality of wavelengths and (ii) an image of fluorescence focused are superimposed.

(Reconstruction of Object Light and Fluorescence)

Figure 5:
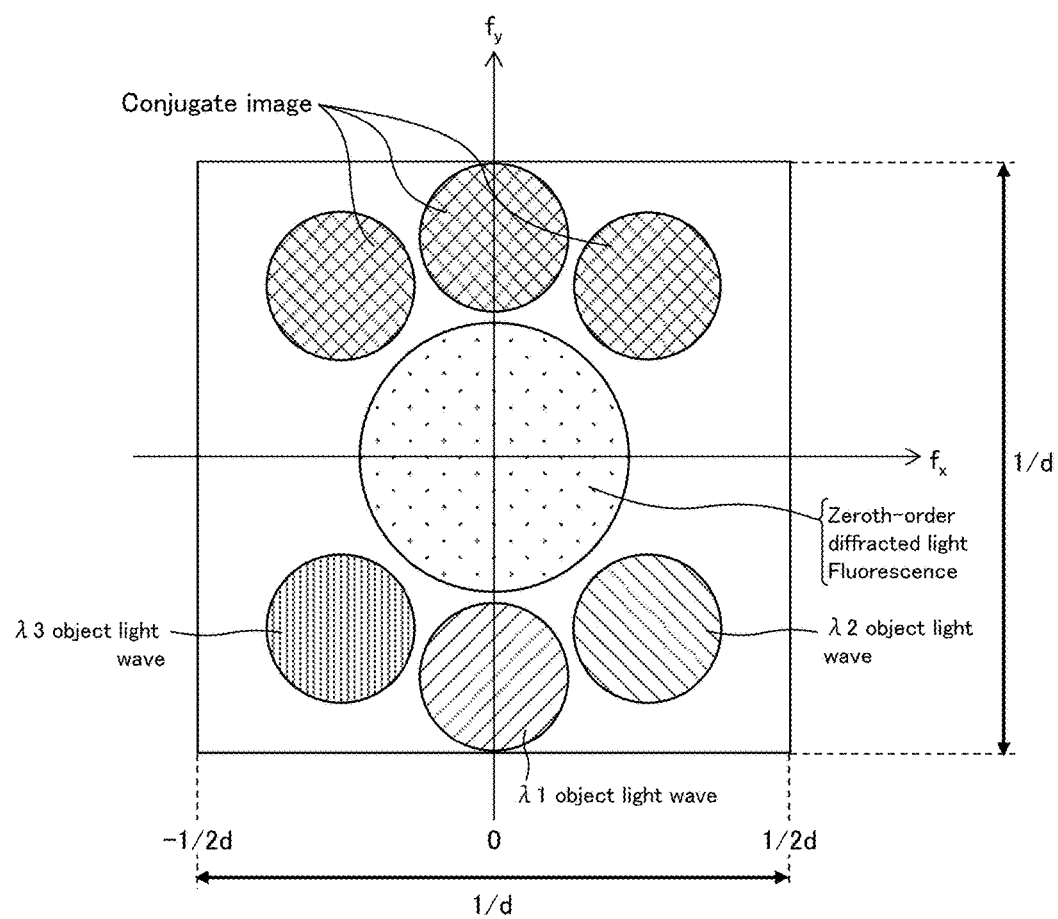
FIG. 5 is a view schematically illustrating an image obtained by subjecting a recorded image to two-dimensional Fourier transform.

FIG. 5 is a view schematically illustrating an image obtained by carrying out two-dimensional Fourier transform on a recorded image. In FIG. 5, a lateral axis represents a spatial frequency fx on an x axis, while a longitudinal axis represents a spatial frequency fy on a y axis.

The reconstruction device 11 subjects the recorded image to two-dimensional Fourier transform to obtain a Fourier-transformed image (FIG. 5). In the spatial frequency plane of the image containing the holograms and the image of the fluorescence, there exist spatial spectrums of zeroth-order diffracted light beams of the wavelengths $\lambda 1$ to $\lambda 3$, spatial spectrums of object light waves (first-order diffracted light beams) of the wavelengths $\lambda 1$ to $\lambda 3$, spatial spectrums of conjugate images (minus first-order diffracted light beams) of the wavelengths $\lambda 1$ to $\lambda 3$, and a spatial spectrum of the fluorescence.

The spatial spectrums of the zeroth-order diffracted light beams of the wavelengths $\lambda 1$ to $\lambda 3$ are distributed around the origin point and are overlaid with each other. Most of the spatial spectrum of the fluorescence is also distributed around the origin point. Therefore, distribution of the spatial spectrums of the zeroth-order diffracted light beams and distribution of the spatial spectrum of the fluorescence are at least partially overlaid with each other.

On the other hand, the spatial spectrums of the object light waves of the wavelengths $\lambda 1$ to $\lambda 3$ appear at mutually different positions according to the incidence angles of the reference light beams having the individual wavelengths (each angle between an optical axis of the object light and an optical axis of the reference light). For example, when the reference light beams incident on the image capturing plane are tilted in the x axis direction, the spatial spectrums of the object light waves appear on a high frequency end of fx. Similarly, when the reference light beams incident on the image capturing plane are tilted in the y axis direction, the spatial spectrums of the object light waves appear on the high frequency end of fy. The recording device 20 is configured such that respective incidence angles of the wavelengths are different so that spatial spectrums of the different object light waves having the wavelengths are separable (are not overlaid).

The reconstruction device 11 extracts, from the Fourier-transformed image, the spatial spectrum of the object light wave for each wavelength. Thus, the reconstruction device 11 can determine, for each wavelength, the complex amplitude of the object light in each pixel based on the extracted spatial spectrum of the object light wave.

The reconstruction device 11 can extract a spatial spectrum of the fluorescence by determining zeroth-order diffracted light components of the wavelengths λ1 to λ3 and then extracting the thus determined zeroth-order diffracted light components of the wavelengths λ1 to λ3 from the Fourier-transformed image. In this manner, even in a case where (i) the holograms corresponding to a plurality of wavelengths and (ii) the image of the fluorescence focused are superimposed, the reconstruction device 11 is capable of separately reconstruct object light beams of the individual wavelengths and fluorescence. The digital holography apparatus 2 is capable of performing color imaging of a three-dimensional shape of the subject 13 and obtaining an (monochrome) image of fluorescence. Further, even in a case where reference light beams of the individual wavelengths are identical in incidence angle, spatial spectrums of object light waves of the individual wavelengths can be separated by taking advantage of the fact that a spatial frequency varies depending on a difference in wavelength. Further, in a case where the spatial spectrums of object light and fluorescence or the spatial spectrums of object light beams of the individual wavelengths partially superimposed, it is possible to extract the spatial spectrums except for the superimposed part and then reconstruct an image.

Embodiment 3

Embodiment 3 describes an arrangement in which laser light sources corresponding to a plurality of wavelengths and a color image capturing device are used.

(Recording of Object Light and Fluorescence)

Figure 6:
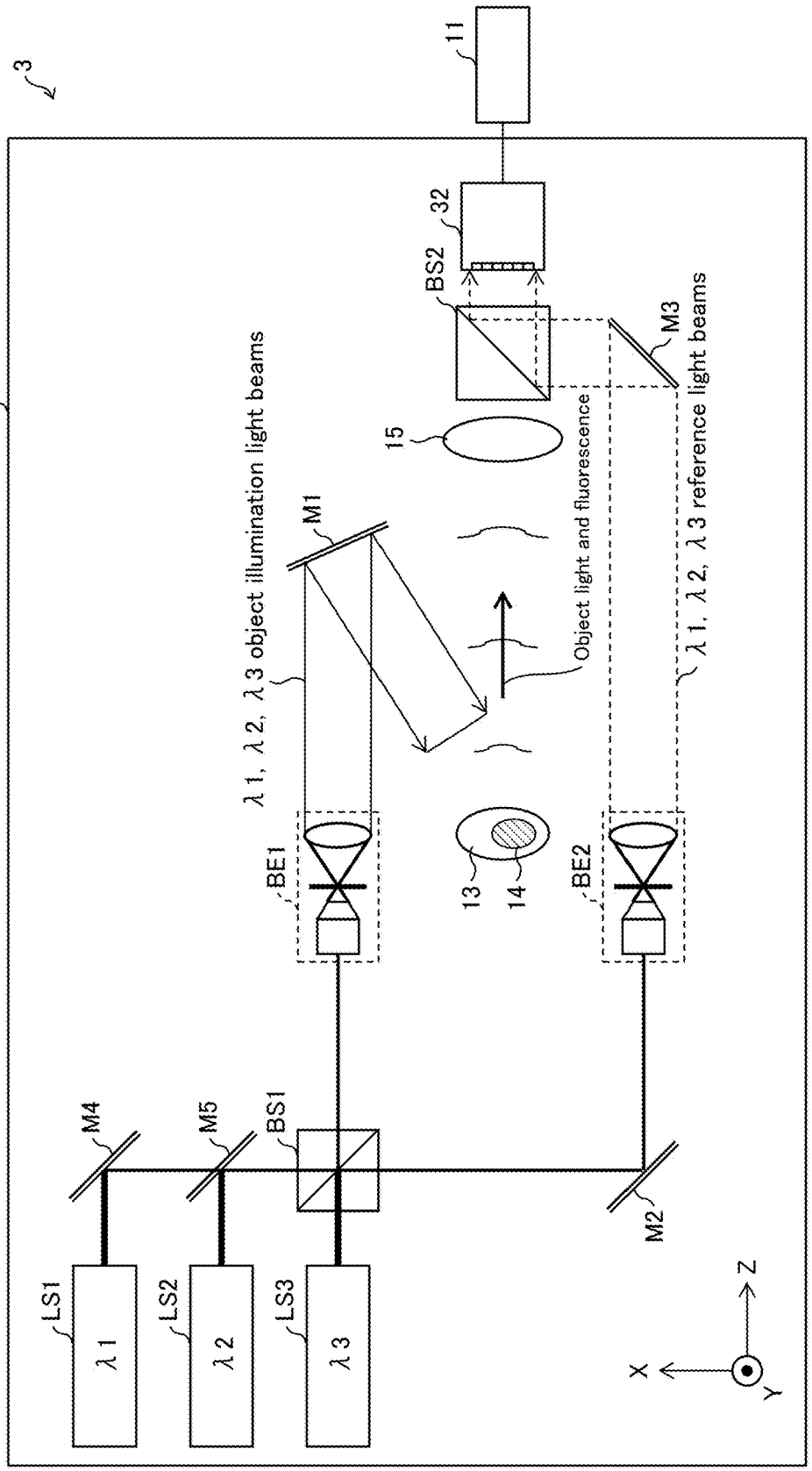
FIG. 6 is a diagram schematically illustrating the configuration of a digital holography apparatus in accordance with still another embodiment of the present invention.

FIG. 6 is a diagram schematically illustrating the configuration of a digital holography apparatus 3 in Embodiment 3. The digital holography apparatus 3 is an off-axis type digital holography apparatus. The digital holography apparatus 3 includes a recording device 30 (digital holography recording device) and a reconstruction device 11. The recording device 30 includes an image capturing device 32, a laser light source LS1 whose wavelength is λ1, a laser light source LS2 whose wavelength is λ2, a laser light source LS3 whose wavelength is λ3, and an optical system.

The optical system, which is provided with a plurality of optical elements such as a mirror, guides laser light (coherent light) having a wavelength λ1, laser light (coherent light) having a wavelength λ2, and laser light (coherent light) having a wavelength λ3 (hereinafter referred to simply as "λ1 laser light", "λ2 laser light", and "λ3 laser light", respectively) to a subject 13 and the image capturing device 32. Specifically, the optical system includes, as the plurality of optical elements, beam splitters BS1 and BS2, mirrors M1 to M5, beam expanders BE1 and BE2, and an image forming element 15.

Paths of object illumination light beams, object light beams, and fluorescence are the same as those in Embodiment 2. In Embodiment 3, unlike Embodiment 2, reference light beams having wavelengths λ1 to λ3 pass through one and the same path and enter the image capturing plane while being aligned coaxially. Note, however, that there is an angle difference between an optical axis of the object light and an optical axis of the reference light.

In Embodiment 3, unlike Embodiment 2, the image capturing device 32 is a color image capturing device. The imaging device 32 captures an image in sub-pixels R (red), an image in the sub-pixels of G (green), and an image in sub-pixels B (blue) to generate a color image. The color image contains information of an R channel, information of a G channel, and information of a B channel, and respective images of the individual colors can be separated from the color image. In this embodiment, it is assumed that light of the wavelength λ1 is recorded only on the R channel, light of the wavelength λ2 is recorded only on the G channel, and the light of the wavelength λ3 is recorded only in the B channel. Fluorescence is recorded on one or more channels in accordance with a wavelength of the fluorescence.

For example, an image on the R channel is a superimposed image in which a hologram corresponding to the wavelength λ1 and an image of fluorescence are superimposed. For example, an image on the G channel is a superimposed image in which a hologram corresponding to the wavelength λ2 and an image of fluorescence are superimposed. For example, an image on the B channel is an image which contains only a hologram corresponding to the wavelength λ3.

The reconstruction device 11 is capable of separating and reconstructing object light of the wavelength λ1 and the fluorescence from the image on the R channel, as in Embodiments 1 and 2. This also applies to the image on the G channel. The reconstruction device 11 is capable of reconstructing object light of the wavelength λ3 from the image on the B channel and consequently obtaining a dark image as an image of fluorescence.

The reconstruction device 11 is capable of obtaining a reconstructed image in color by synthesizing reconstructed images of R, G, and B for object light or fluorescence. The digital holography apparatus 3 is capable of performing color imaging of a three-dimensional shape of the subject 13 and obtaining a color image of fluorescence. Even in a case where the image on the B channel, as is the case with the image on the R channel and the image on the G channel, is a superimposed image in which a hologram corresponding to the wavelength λ3 and an image of the fluorescence are superimposed, the reconstruction device 11 is capable of, as a matter of course, obtaining a color image of fluorescence in a similar manner.

Embodiment 4

Embodiment 4 describes a reconstruction method in which Fourier transform is not used. The reconstruction device 11 in accordance with Embodiment 4 determines a complex amplitude of object light by using a spatial phase shift method in a case where a phase of reference light is spatially different (phase of the reference light varies from pixel to pixel on the image capturing plane). Note that a recording device can be configured as in Embodiment 1. The following describes specifics.

(Recording Device)

(a) of FIG. 20 is a diagram schematically illustrating a relationship between (i) pixels of the image capturing device and (ii) reference light, and (b) of FIG. 20 is a diagram schematically illustrating phase shift amounts of the reference light in part of an image capturing plane (or a recorded image) in the image capturing device. One square in (b) of FIG. 20 corresponds to one pixel.

On the image capturing plane of the image capturing device, a plurality of pixels 12a are arranged. For example, in a case where the reference light is tilted in the x axis direction with respect to the z axis, a phase of reference light in the x-axis direction is different for each of the pixels 12a. For example, assuming that the incident angle θ on a x-z plane satisfies 4d·sin θ=λ, the pixels are arranged along the x axis direction such that phases of reference light are 0, π/2, π, and 3π/2 where the phase of reference light at a certain pixel 12a is referenced as 0. The symbol d is a pixel pitch. The phase shift from this reference is called a phase shift amount. Similarly, phases of reference light in a hologram of a recorded image are shifted by phase shift amounts as shown in (b) of FIG. 20.

Note that when the optical axis of the reference light is tilted both in the x axis direction and in the y axis direction, phase shifts of the reference light increase or decrease accordingly. The difference in phase shift amount is not limited to π/2. Further, in an in-line type optical system in which an optical axis of object light and an optical axis of reference light are aligned, it is possible to obtain a recorded image of a phase distribution of reference light as shown in (c) of FIG. 20, by using, for example, a spatial light modulator array, an array of phase-shifting elements such as a glass or a wave plate, a diffraction element which causes the Talbot effect, or a polarizer array. Alternatively, instead of causing phase shifts of the reference light, phase shifts of the object light can be caused by tilting the optical axis of the object light or by providing an array of phase shift elements in a path of the object light.

(Reconstruction Device)

FIG. 21 is a view illustrating a flow of a reconstruction process carried out by a reconstruction device 11 of Embodiment 4. FIG. 22 is a diagram showing an outline of a flow of the reconstruction process. In FIG. 22, squares represent pixels in an enlarged part of an image, and a numerical value in each of the squares represents a phase shift amount. The following description takes, as an example, a case where a difference in phase shift amount between adjacent pixels in the x axis direction (horizontal direction) is 2π/3. The recorded image records a hologram formed by interference between the object light and the phase-shifted reference light and an image of fluorescence in a state in which the hologram and the image of the fluorescence are superimposed.

The reconstruction device 11 extracts, from the recorded image, pixels which correspond to an identical one of the phase shift amounts to thereby obtain a plurality of images which are in a one-to-one correspondence with the individual phase shift amounts. The reconstruction device 11 interpolates the images thus obtained to bridge gaps in pixel value between the pixels so that a plurality of interpolated images are obtained (S11).

The reconstruction device 11 uses a spatial phase shift method to obtain a complex amplitude distribution of the object light from the plurality of interpolated images which are different in phase shift amount from each other (S12). In so doing, it is possible to use a known formula of the spatial phase shift method for determining a complex amplitude of object light only from a hologram. The reconstruction device 11 can obtain a reconstructed image of a subject from the complex amplitude distribution of the object light.

The reconstruction device 11 determines a distribution of the light intensity Ih of the hologram from the complex amplitude distribution of the object light, a known reference light intensity distribution, and the phase shift amounts of the reference light (S13). The reconstruction device 11 obtains an image of fluorescence by subtracting the light intensity distribution of the hologram from the recording image (removal of the hologram) (S14). In this way, the reconstruction device 11 can reconstruct the object light and the image of the fluorescence from the recorded image in which the hologram and the image of the fluorescence are superimposed.

The Fourier transform process is a computationally intensive process. According to Embodiment 4, the reconstruction process eliminates the need for the Fourier transform. This enables separation and reconstruction of the object light and the image of the fluorescence at a high speed. Therefore, the reconstruction device 11 of Embodiment 4 enables real-time moving image reconstruction of the object light and the image of the fluorescence.

Modification

The above description has discussed the example case in which pixels are extracted and interpolated. The following description discusses a case where separation and reconstruction of object light and an image of fluorescence are carried out, without any interpolation process, for the purpose of achieving further reduction of load on the reconstruction process.

FIG. 23 is a diagram showing phase shift amounts of reference light in an enlarged part of a recorded image. When the optical axis of the reference light is tilted both in the x axis direction and in the y axis direction, a distribution of phase shift amounts of the reference light becomes the one as shown in FIG. 23.

A pixel value I(x,y) of the recorded image is a sum of the light intensity If(x,y) of the image of the fluorescence and the light intensity Ih(x,y) of the hologram. The symbols x and y denote coordinates of a pixel.

$$I(x,y)=If(x,y)+Ih(x,y) \quad (2)$$

$$Ih(x,y)=|Uo(x,y)|^2+|Ur(x,y)|^2+ \\ 2Ao(x,y)Ar(x,y)\cos\{\varphi o(x,y)-\varphi r(x,y)\} \quad (3)$$

where the complex amplitude of the object light is given by $Uo(x,y)=Ao(x,y)\exp\{j\varphi o(x,y)\}$, and the complex amplitude of the reference light is given by $Ur(x,y)=Ar(x,y)\exp\{j\varphi r(x,y)\}$. The symbols Ao and Ar denote amplitudes. The symbols φo and φr denote phases. The symbol j is an imaginary unit. Let M the number of pixels in the x axis direction and N the number of pixels in the y axis direction. In this case, $0 \leq x \leq M-1$ and $0 \leq y \leq N-1$ (where x and y are pixel addresses (integers)).

The reconstruction device 11 uses the spatial phase shift method to calculate the complex amplitude of the object light by using the value of a certain pixel located near a target pixel (x,y). Specifically, the object light of the target pixel is calculated based on the following equations.

When a remainder of 0 is given by division of (x+y) by 4, $$Uo(x,y)=[\{I(x,y)-I(x+1,y+1)\}+j\{I(x+1,y)+ \\ I(x,y+1)-I(x,y)-I(x+1,y+1)\}]/\{4Ar(x,y)\} \quad (4)$$

When a remainder of 1 is given by division of (x+y) by 4, $$Uo(x,y)=[\{I(x+1,y)+I(x,y+1)-I(x,y)- \\ I(x+1,y+1)\}+j\{I(x,y)-I(x+1,y+1)\}]/\{4Ar(x,y)\} \quad (5)$$

When a remainder of 2 is given by division of (x+y) by 4, $$Uo(x,y)=[-\{I(x,y)-I(x+1,y+1)\}-j\{I(x+1,y)+ \\ I(x,y+1)-I(x,y)-I(x+1,y+1)\}]/\{4Ar(x,y)\} \quad (6)$$

When a remainder of 3 is given by division of (x+y) by 4, $$Uo(x,y)=[\{I(x+1,y)+I(x,y+1)-I(x,y)-I(x+1,y+1)\}-j\{I(x,y)-I(x+1,y+1)\}]/\{4Ar(x,y)\} \quad (7)$$

This allows the reconstruction device 11 to determine the complex amplitude of the object light. The reconstruction device 11 determines the distribution of the light intensity Ih of the hologram from the complex amplitude distribution of the object light, a known intensity distribution of the reference light, and the phase shift amounts of reference light (phases of reference light). By subtracting the light intensity Ih of the hologram from the pixel value I of the recorded image by the equation (2), the reconstruction device 11 determines the light intensity Ih of the image of the fluorescence. Further, in a case where the intensity distribution of the reference light is uneven, it is possible to carry out the calculation based on the spatial phase shift method after the intensity distribution of the reference light is subtracted from the recorded image. This makes it possible to alleviate the problem of image quality degradation of an image to be outputted due to unevenness of the intensity of the reference light.

According to this modification, it is unnecessary to perform Fourier transform and a pixel interpolation process. This makes it possible to further reduce load on the reconstruction process and to carry out reconstruction at a higher speed.

[Simulation 1]

The following description discusses a result of a simulation of hologram recording and reconstruction according to Embodiment 1 of the present invention. This simulation is assumed to use the digital holography apparatus 1 illustrated in FIG. 1.

Figure 7:
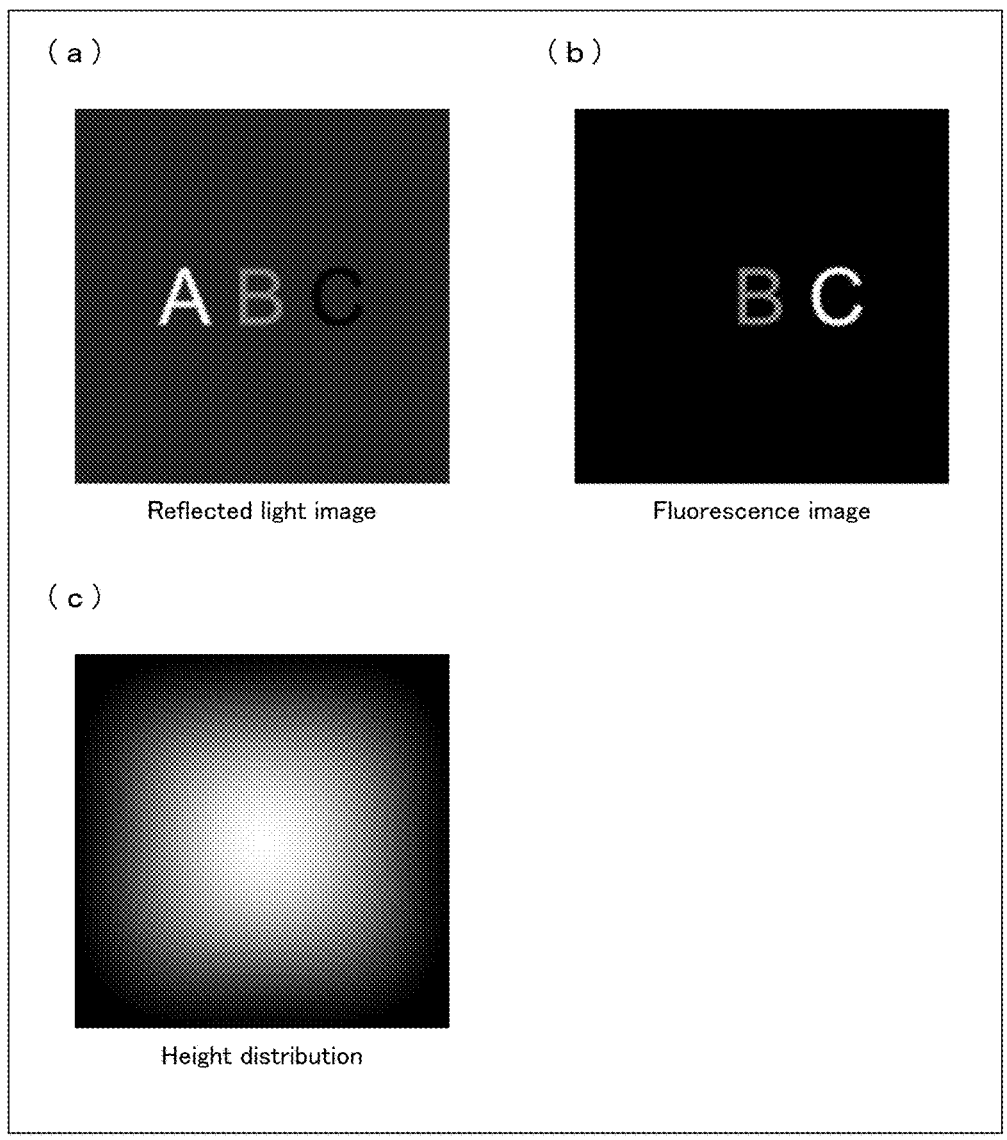
FIG. 7 shows a subject to be used in the simulation based on an embodiment of the present invention.
Figure 8:
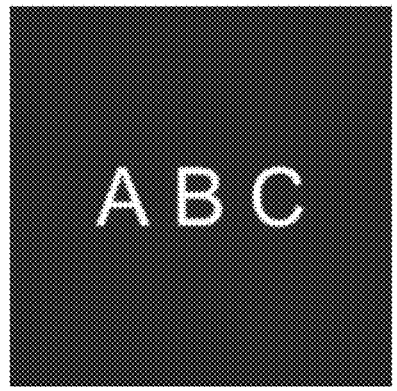
FIG. 8 shows an image of the subject perceived through a normal camera.

FIG. 7 shows a subject to be used in the simulation. (a) of FIG. 7 shows a reflected light image of the subject (image of object light of the wavelength $\lambda 1$), (b) of FIG. 7 shows an image of fluorescence of the subject, and (c) of FIG. 7 shows a height distribution of the subject. For example, an area where the character "C" is located hardly reflects the object light of the wavelength $\lambda 1$ but strongly emits fluorescence. When the subject is observed through a normal camera or in human eyes, an image shown in FIG. 8 is perceived, and reflected light (object light) and fluorescence cannot be identified separately. Note that, in (c) of FIG. 7, the height of the subject (height which extends to the image capturing device in the z direction) is expressed by brightness. A bright area is greater in height than a dark area.

Conditions of the simulation are as follows. The wavelength of a light source is $\lambda=532$ nm. The image capturing element has 2048 pixels wide by 2048 pixels long, and a pixel pitch is 2.2 µm widthwise and 2.2 µm lengthwise. On the assumption that this simulation uses an off-axis type hologram recording arrangement, the incidence angle of reference light is $6.05 \times 10^{-2}$ rad from the z axis to the x axis (on the x-z plane) and $6.05 \times 10^{-2}$ rad from the z axis to the y axis (on the y-z plane). The intensity ratio between object illumination light and reference light is 1:1. An image of reference light intensity distribution is recorded before or after the measurement. Intensities of reflected light and fluorescence are 0 to 255 (the number of gray levels is 256). A maximum height of the object is 200 nm. To obtain reflected light and fluorescence through the use of a single light source, the following conditions are provided in this simulation. A total amount of energy of reflected light and fluorescence is smaller than the amount of energy of object illumination light. Light emitted from a single light source functions as excitation light and also functions to generate reflected light and a hologram of the reflected light. Further, there is provided no object light-blocking or fluorescence-blocking filter for separating object light and fluorescence. Thus, bright image recording without loss of fluorescence light quantity due to a filer can be expected.

Under the above conditions, the simulation was performed by a calculator to record a recorded image shown in (a) of FIG. 9 and calculate a reconstructed image through the use of the reconstruction device 11. Note that hologram recording was also performed by a calculator simulation. A recorded image is a superimposed image in which a hologram and an image of fluorescence are superimposed. (b) of FIG. 9 shows an enlarged part of the recorded image. As shown in (b) of FIG. 9, interference fringes (hologram) are recorded on the recorded image.

By subjecting the recorded image shown in (a) of FIG. 9 to Fourier transform, an image shown in (a) of FIG. 10 (Fourier-transformed image) is obtained. A component of reflected light, which component is recorded as a hologram, can be obtained separately from a component of a fluorescence image. An image obtained by extracting a spatial spectrum (circled area at the lower right in (a) of FIG. 10) of the reflected light component from the Fourier-transformed image is subjected to inverse Fourier transform. Based on a resulting inverse Fourier-transformed image, a reflected light image (reconstructed image) shown in (b) of FIG. 10 and a phase distribution shown in (c) of FIG. 10 are determined. The phase distribution is expressed by a phase of light corresponding to the height of the subject. Since the phase distribution includes three-dimensional shape information, height information of the subject can be recognized from (c) of FIG. 10.

Next, as shown in FIG. 11, the zeroth-order diffracted light component is subtracted from the recorded image (in (a) of FIG. 9), and a resulting image is then subjected to Fourier transform. As a result, an image shown in (a) of FIG. 12 is obtained. Unlike the Fourier-transformed image (in (a) of FIG. 10) obtained without subtracting the zeroth-order diffracted light component, the Fourier-transformed image shown in (a) of FIG. 12 has a spatial spectrum whose distribution in the center of the image is changed. This indicates that with the removal of the zeroth-order diffracted light component, only the spatial spectrum of the fluorescence image remains in the center of the image. That is, from the Fourier-transformed image shown in (a) of FIG. 12, only the spatial spectrum (circled area in the center of (a) of FIG. 12) of the fluorescence image is extracted, and the extracted spatial spectrum is subjected to inverse Fourier transform. As a result, a fluorescence image (reconstructed image) shown in (b) of FIG. 12 was obtained.

To perform quantitative evaluation, a mean square error, a cross-correlation function, and a signal-to-noise ratio of the reconstructed image relative to the original image (in FIG. 7) were calculated. The mean square error of the reflected light image (reconstructed image) was $8.6 \times 10^{-2}$, the cross-correlation function thereof was 1.00, and the signal-to-noise ratio thereof was 56 dB. The mean square error of the fluorescence image (reconstructed image) was $8.5 \times 10^{-2}$, the cross-correlation function thereof was 1.00, and the signal-to-noise ratio thereof was 48 dB. The mean square error of the height distribution (phase distribution) was $2.7 \times 10^{-2}$ nm, the cross-correlation function thereof was 1.00, and the signal-to-noise ratio thereof was 79 dB. As described above, a reflected light image of a moment of a dynamic object, a fluorescence image thereof, and three-dimensional shape information thereof are obtained with a high degree of accuracy by a recording device with a single light source.

[Simulation 2]

The following description discusses a result of a simulation of hologram recording and reconstruction according to Embodiment 3 of the present invention. This simulation is assumed to use the digital holography apparatus 3 illustrated in FIG. 6.

FIG. 13 shows a reflected light image of a subject to be used in the simulation. (a) of FIG. 13 shows a R (red) channel image of reflected light of the subject, (b) of FIG. 13 shows a G (green) channel image of the reflected light of the subject, (c) of FIG. 13 shows a B (blue) channel image of the reflected light of the subject, and (d) of FIG. 13 shows a reflected light image, of the subject, obtained by RGB color composition. In (d) of FIG. 13, each color is displayed in a single color (gray), and components of R and B in a color composite image look thinner. However, the image shown in (d) of FIG. 13 is a composite image produced by compositing the images in the respective colors. The same applies to other color composite image.

FIG. 14 shows a fluorescence image of a subject to be used in the simulation. (a) of FIG. 14 shows a R channel fluorescence image of the subject, (b) of FIG. 14 shows a G channel fluorescence image of the subject, (c) of FIG. 14 shows a B channel fluorescence image of the subject, and (d) of FIG. 14 shows a fluorescence image, of the subject, obtained by RGB color composition.

FIG. 15 shows a height distribution of the subject. In FIG. 15, the height of the subject is expressed by brightness. When the subject is observed through a normal camera or in human eyes, an image shown in FIG. 16 is perceived, and reflected light (object light) and fluorescence cannot be identified separately.

Conditions of the simulation are as follows. The wavelengths of a light source are $\lambda 1$=640 nm, $\lambda 2$=532 nm, and $\lambda 3$=473 nm. A color image sensor equipped with a Bayer type color filter array is used as the image capturing device 32. Each channel of the color filter array blocks light beams of any two wavelengths out of light beams of the three wavelengths $\lambda 1$, $\lambda 2$, and $\lambda 3$. The image capturing element has 2048 pixels wide by 2048 pixels long, and a pixel pitch is 1.4 µm widthwise and 1.4 µm lengthwise. On the assumption that this simulation uses an off-axis type hologram recording arrangement, the incidence angle of reference light is $6.05 \times 10^{-2}$ rad to the x axis and $6.05 \times 10^{-2}$ rad to the y axis. The intensity ratio between object illumination light and reference light is 1:1. An image of reference light intensity distribution corresponding to each wavelength is independently recorded for each wavelength before or after the measurement. Intensities of a reflected light beam and fluorescence are 0 to 255 (the number of gray levels is 256). A maximum height of the subject is 240 nm. It is assumed that reflected light beams are obtained from light beams originating from the individual light sources, and light beams from two of the three light sources excite a fluorescent material. In this simulation, a total amount of energy of a reflected light beam and fluorescence in each light source is smaller than the amount of energy of object illumination light. Further, it is assumed that a reflected light beam and a corresponding fluorescence have wavelengths equal to each other. For example, the conditions where fluorescence generated from $\lambda 3$ and a reflected light beam from $\lambda 1$ contain components equal in wavelength are assumed. That is, the conditions where a reflected light beam and fluorescence cannot be separated by a wavelength filter are assumed. Note that the object illumination light of the wavelength $\lambda 3$ leads to generation of cyan fluorescence (character "A"), yellow-green fluorescence (character "0"), yellow fluorescence (character "B"), and red fluorescence (characters "1" and "2"). The object illumination light of the wavelength $\lambda 2$ leads to generation of yellow-green fluorescence, yellow fluorescence, and red fluorescence. The object illumination light of the wavelength $\lambda 1$ does not excite the fluorescent material.

Under the above conditions, the simulation was performed by a calculator to record recorded images of RGB on the respective channels of the color image sensor and calculate a reconstructed image. Note that hologram recording was also performed by a calculator simulation. Each recorded image is a superimposed image in which a hologram and an image of fluorescence are superimposed.

From the recorded images, of the individual colors, recorded on RGB channels of the color image sensor, a reflected light image, a fluorescence image, and a height distribution (phase distribution) are reconstructed for each color through a procedure similar to that in the simulation 1. From the R channel recorded image, images shown in FIG. 17 were obtained. From a G channel recorded image, images shown in FIG. 18 were obtained. From a B channel recorded image, images shown in FIG. 19 were obtained.

(a) of FIG. 17 shows a reflected light image (reconstructed image) obtained from a R channel recorded image, (b) of FIG. 17 shows a fluorescence image (reconstructed image) obtained from the R channel recorded image, and (c) of FIG. 17 shows a phase distribution obtained from the R channel recorded image. (a), (b), and (c) of FIG. 18 show a reflected light image (reconstructed image), a fluorescence image (reconstructed image), and a phase distribution, respectively, obtained from the G channel recorded image. (a), (b), and (c) of FIG. 19 show a reflected light image (reconstructed image), a fluorescence image (reconstructed image), and a phase distribution, respectively, obtained from the B channel recorded image. In phase distributions in (c) of FIG. 18 and in (c) of FIG. 19, phase folding (change from light to dark at a position where a phase exceeds $2\pi$) occurs. This causes a dark area in the center in (c) of FIG. 18 and (c) of FIG. 19. Even from these phase distributions, three-dimensional shape information can be obtained by performing phase unwrapping.

It can be seen that reflected light and fluorescence were separated and reconstructed for each channel, and information on height distribution (three-dimensional shape) is also obtained. To perform quantitative evaluation, a mean square error, a cross-correlation function, and a signal-to-noise ratio of a reconstructed image for each channel relative to the original image (FIGS. 13 to 15) were calculated. The mean square error of the R channel reflected light image was $5.8 \times 10^{-1}$, the cross-correlation function thereof was 1.00, and the signal-to-noise ratio thereof was 30 dB. The mean square error of the R channel fluorescence image was $9.6 \times 10^{-1}$, the cross-correlation function thereof was 1.00, and the signal-to-noise ratio thereof was 29 dB. The mean square error of the G channel reflected light image was $6.0 \times 10^{-1}$, the cross-correlation function thereof was 1.00, and the signal-to-noise ratio thereof was 31 dB. The mean square error of the G channel fluorescence image was 1.0, the cross-correlation function thereof was 1.00, and the signal-to-noise ratio thereof was 30 dB. The mean square error of the B channel reflected light image was $6.9 \times 10^{-1}$, the cross-correlation function thereof was 1.00, and the signal-to-noise ratio thereof was 30 dB. The mean square error of the B channel fluorescence image was $5.9 \times 10^{-1}$, the cross-correlation function thereof was 1.00, and the signal-to-noise ratio thereof was 29 dB. The mean square error of the height distribution (phase distribution) was $3.4 \times 10^{-1}$ nm, the cross-correlation function thereof was 1.00, and the signal-to-noise ratio thereof was 58 dB. As described above, a reflected light image of a moment of a dynamic object, a color fluorescence image thereof, and three-dimensional shape information thereof are obtained.

[Simulation 3]

The following description discusses a result of a simulation of hologram recording and reconstruction according to Embodiment 4 of the present invention. This simulation is assumed to use the digital holography apparatus 1 illustrated in FIG. 1.

A subject used in the simulation (reflected light image, fluorescence image, and height distribution) is the same as that used in the simulation 1 (FIG. 7). The conditions for the simulation of recording are also the same as those for the simulation 1. That is, the recorded image used in this simulation is the same as that used in the simulation 1 (FIG. 9).

Under the above conditions, the simulation was performed by a calculator to record a recorded image shown in (a) of FIG. 9 and calculate a reconstructed image through the use of the reconstruction device 11. Note that hologram recording was also performed by a calculator simulation. A recorded image is a superimposed image in which a hologram and an image of fluorescence are superimposed.

Through the use of the reconstruction device 11, a complex amplitude (distribution) of object light was determined from the recorded image by using the spatial phase shift methods (the above equations (4) to (7)). (a) of FIG. 24 shows a reflected light image (reconstructed image) of a subject which image was obtained by reconstruction using the complex amplitude of the object light, and (b) of FIG. 24 shows a phase distribution calculated by using the complex amplitude of the object light. A reflected light image and a phase distribution component (information of object light) are recorded as a hologram and can be obtained separately from a fluorescence image when they are subjected to signal processing based on the spatial phase shift method. Since the phase distribution includes three-dimensional shape information, height information of the subject can be recognized from (b) of FIG. 10.

Through the use of the reconstruction device 11, an image of the hologram (light intensity of the hologram) was determined based on the complex amplitude of the object light, intensity distribution of reference light, and a phase of the reference light. Then, the image of the hologram was subtracted from the recorded image to obtain a fluorescence image (reconstruction) shown in FIG. 25. This corresponds to a process of removing a hologram component from a recorded image in which a hologram and an image of fluorescence are superimposed. In this manner, through the use of the reconstruction device 11, it was possible to separately reconstruct the reflected light image (a reconstructed image of object light) and the fluorescence image from the recorded image in which the hologram and the image of fluorescence are superimposed.

To perform quantitative evaluation, a mean square error, a cross-correlation function, and a signal-to-noise ratio of the reconstructed image relative to the original image (in FIG. 7) were calculated. The mean square error of the reflected light image was $5.8 \times 10^{-1}$, the cross-correlation function thereof was 0.999, and the signal-to-noise ratio thereof was 39 dB. The mean square error of the fluorescence image was $7.5 \times 10^{-1}$, the cross-correlation function thereof was 0.999, and the signal-to-noise ratio thereof was 29 dB. The mean square error of the height distribution (phase distribution) was $3.4 \times 10^{-1}$ nm, the cross-correlation function thereof was 1.00, and the signal-to-noise ratio thereof was 57 dB. As described above, a reflected light image of a moment of a dynamic object, a fluorescence image thereof, and three-dimensional shape information thereof are obtained with a high degree of accuracy by a recording device with a single light source.

[Software Implementation Example]

The processing of the reconstruction device 11 can be realized by a logic circuit (hardware) provided in an integrated circuit (IC chip) or the like or can be alternatively realized by software as executed by a central processing unit (CPU).

In the latter case, the reconstruction device 11 includes: a CPU that executes instructions of a program that is software realizing the foregoing functions; a read only memory (ROM) or a storage device (each referred to as "storage medium") in which the program and various kinds of data are stored so as to be readable by a computer (or a CPU); and a random access memory (RAM) in which the program is loaded. An object of the present invention can be achieved by a computer (or a CPU) reading and executing the program stored in the storage medium. Examples of the storage medium encompass "a non-transitory tangible medium" such as a tape, a disk, a card, a semiconductor memory, and a programmable logic circuit. The program can be supplied to the computer via any transmission medium (such as a communication network or a broadcast wave) which allows the program to be transmitted. Note that the present invention can also be achieved in the form of a computer data signal in which the program is embodied via electronic transmission and which is embedded in a carrier wave.

[Recap]

A digital holography recording device in accordance with an aspect of the present invention includes: a light source which irradiates an object with object illumination light so that object light is generated; and an image capturing device which captures (i) a hologram formed by interference between reference light and the object light and (ii) an image of fluorescence, the object illumination light further exciting a fluorescent material contained in the object.

The above configuration enables both the hologram and the image of the fluorescence to be simultaneously captured in a state in which they can be reconstructed separately. Further, the object illumination light emitted from one light source functions to generate object light and also functions to be excitation light for exciting the fluorescent material. Thus, the digital holography recording device has an advantage in its suitability for downsizing.

The light source may be configured to emit the object illumination light of a single wavelength.

The image capturing device may be configured to capture a superimposed image in which (i) the hologram formed by interference between the object light and the reference light and (ii) the image of the fluorescence emitted by the fluorescent material are superimposed.

The digital holography recording device may be configured to further include: an image-forming optical element which images the fluorescence on an image capturing plane of the image capturing device.

The above configuration enables reconstruction of an image of focused fluorescence based on a recorded image.

The image capturing device may be a monochromatic image capturing device using no color filter.

The above configuration enables separation and reconstruction of object light and fluorescence without using a color filter. Further, the image capturing device can record a bright image without loss of fluorescence light quantity due to a color filer.

The digital holography recording device may be configured such that the light source is a first light source which irradiates the object with object illumination light of a first wavelength, and the digital holography recording device further includes: a second light source which irradiates the object with object illumination light of a second wavelength, which is different from the first wavelength, so that object light of the second wavelength is generated, the image capturing device capturing a hologram corresponding to the first wavelength, a hologram corresponding to the second wavelength, and the image of the fluorescence, both the object illumination light of the first wavelength and the object illumination light of the second wavelength, exciting the fluorescent material.

The above configuration enables a plurality of holograms to be obtained based on object light beams having two different wavelengths and thus enables spectroscopic measurement of the object. The above configuration also enables the fluorescent material to be excited by object illuminating light beams having two different wavelengths. This enables enhancement in intensity of fluorescence emitted from the fluorescent material.

The digital holography recording device may be configured such that an optical axis of the reference light incident on the image capturing device is tilted with respect to an optical axis of the object light incident on the image capturing device.

The above configuration enables accurate extraction of the spatial spectrum of the object light wave in the spatial frequency plane of the recorded image. This enables increase in accuracy of reconstruction of object light.

A digital holography recording device in accordance with an aspect of the present invention includes: a light source which irradiates an object with object illumination light; and an image capturing device which captures a superimposed image in which (i) a hologram formed by interference between reference light and object light from the object and (ii) an image of fluorescence emitted by a fluorescent material contained in the object are superimposed.

The above configuration enables both the hologram and the image of the fluorescence to be simultaneously captured in a state in which they can be reconstructed separately.

A digital holography reconstruction device in accordance with an aspect of the present invention operates to: use a spatial phase shift method to determine a complex amplitude of object light based on a superimposed image in which (i) a hologram formed by interference between reference light and the object light and (ii) an image of fluorescence are superimposed; determine an intensity (light intensity distribution) of the hologram based on the complex amplitude of the object light; and remove the hologram from the superimposed image (subtract the light intensity distribution of the hologram) to obtain (an image representing) the image of the fluorescence.

The above configuration enables information of object light and information of fluorescence to be separated at a high speed from a superimposed image in which the hologram and the image of the fluorescence are superimposed.

A digital holography reconstruction device in accordance with an aspect of the present invention operates to: subject, to Fourier transform, a superimposed image in which (i) a hologram formed by interference between reference light and object light and (ii) an image of fluorescence are superimposed; extract a spatial spectrum of the object light from a Fourier-transformed image; subject the extracted spatial spectrum of the object light to inverse Fourier transform to determine a complex amplitude of the object light; determine a zeroth-order diffracted light component based on the complex amplitude of the object light and then remove the zeroth-order diffracted light component from the Fourier-transformed image; and extract, from the Fourier-transformed image from which the zeroth-order diffracted light component has been removed, a spatial spectrum of the image of the fluorescence.

The above configuration enables information of object light and information of fluorescence to be separated accurately from a superimposed image in which the hologram and the image of the fluorescence are superimposed.

The digital holography reconstruction device may be configured such that the image of the fluorescence is obtained by subjecting, to inverse Fourier transform, the extracted spatial spectrum of the image of the fluorescence.

The above configuration enables the object light and the image of the fluorescence to be separately reconstructed based on a superimposed image in which the hologram and the image of the fluorescence are superimposed.

A digital holography reconstruction device in accordance with an aspect of the present invention operates to: subject, to Fourier transform, a superimposed image in which (i) a hologram formed by interference between reference light and object light and (ii) an image of fluorescence are superimposed; extract a spatial spectrum of the object light from a Fourier-transformed image; subject the extracted spatial spectrum of the object light to inverse Fourier transform to determine a complex amplitude of the object light; and determine an intensity of the hologram based on the complex amplitude of the object light and then remove the hologram from the superimposed image to obtain the image of the fluorescence.

A digital holography recording method in accordance with an aspect of the present invention includes the steps of: irradiating an object with object illumination light emitted from a light source so that object light is generated and exciting a fluorescent material contained in the object with the object illumination light; and capturing (i) a hologram formed by interference between reference light and the object light and (ii) an image of fluorescence emitted by the fluorescent material.

A digital holography recording method in accordance with an aspect of the present invention includes the steps of: irradiating an object with object illumination light; and capturing a superimposed image in which (i) a hologram formed by interference between reference light and object light from the object and (ii) an image of fluorescence emitted by a fluorescent material contained in the object are superimposed.

A digital holography reconstruction method in accordance with an aspect of the present invention includes the steps of: using a spatial phase shift method to determine a complex amplitude of object light based on a superimposed image in which (i) a hologram formed by interference between reference light and the object light and (ii) an image of fluorescence are superimposed; determining an intensity of the hologram based on the complex amplitude of the object light; and removing the hologram from the superimposed image to obtain the image of the fluorescence.

A digital holography reconstruction method in accordance with an aspect of the present invention includes the steps of: subjecting, to Fourier transform, a superimposed in which (i)

a hologram formed by interference between reference light and object light and (ii) an image of fluorescence are superimposed; extracting a spatial spectrum of the object light from a Fourier-transformed image; subjecting the extracted spatial spectrum of the object light to inverse Fourier transform to determine a complex amplitude of the object light; determining a zeroth-order diffracted light component based on the complex amplitude of the object light and then removing the zeroth-order diffracted light component from the Fourier-transformed image; and extracting, from the Fourier-transformed image from which the zeroth-order diffracted light component has been removed, a spatial spectrum of the image of the fluorescence.

A digital holography reconstruction method in accordance with an aspect of the present invention includes the steps of: subjecting, to Fourier transform, a superimposed image in which (i) a hologram formed by interference between reference light and object light and (ii) an image of fluorescence are superimposed; extracting a spatial spectrum of the object light from a Fourier-transformed image; subjecting the extracted spatial spectrum of the object light to inverse Fourier transform to determine a complex amplitude of the object light; and determining an intensity of the hologram based on the complex amplitude of the object light and then removing the hologram from the superimposed image to obtain the image of the fluorescence.

The present invention is not limited to the embodiments, but can be altered by a skilled person in the art within the scope of the claims. An embodiment derived from a proper combination of technical means each disclosed in a different embodiment is also encompassed in the technical scope of the present invention.

INDUSTRIAL APPLICABILITY

The present invention is applicable to, for example, a digital holography apparatus, a high-speed 3D camera, and a fluorescence three-dimensional microscope.

REFERENCE SIGNS LIST 1 to 3 Digital holography device
10, 20, 30 Recording device (digital holography recording device)
11 Reconstruction device (digital holography reconstruction device)
12, 32 Image capturing device
13 Subject (object)
14 Fluorescent material
15 Image forming element (image-forming optical element)
LS1 to LS3 Laser light source (first light source, second light source)

The invention claimed is:

1. A digital holography recording device comprising:
a light source which irradiates an object with object illumination light so that object light is generated; and
an image capturing device which simultaneously captures a hologram and an image of fluorescence, the hologram formed by interference between reference light and the object light and reflecting a phase shift amount which varies across pixels and is determined by the reference light and the object light,
the object illumination light further exciting a fluorescent material contained in the object.

2. The digital holography recording device according to claim 1, wherein the light source emits the object illumination light of a single wavelength.

3. The digital holography recording device according to claim 1, wherein the image capturing device captures a superimposed image in which (i) the hologram formed by interference between the object light and the reference light and (ii) the image of the fluorescence emitted by the fluorescent material are superimposed.

4. The digital holography recording device according to claim 3, further comprising:
an image-forming optical element which images the fluorescence on an image capturing plane of the image capturing device.

5. The digital holography recording device according to claim 1, wherein the image capturing device is a monochromatic image capturing device using no color filter.

6. The digital holography recording device according to claim 1, wherein the light source is a first light source which irradiates the object with object illumination light of a first wavelength,
said digital holography recording device further comprising:
a second light source which irradiates the object with object illumination light of a second wavelength, which is different from the first wavelength, so that object light of the second wavelength is generated,
the image capturing device capturing a hologram corresponding to the first wavelength, a hologram corresponding to the second wavelength, and the image of the fluorescence,
both the object illumination light of the first wavelength and the object illumination light of the second wavelength, exciting the fluorescent material.

7. The digital holography recording device according to claim 1, wherein an optical axis of the reference light incident on the image capturing device is tilted with respect to an optical axis of the object light incident on the image capturing device.

8. A digital holography recording device comprising:
a light source which irradiates an object with object illumination light; and
an image capturing device which simultaneously captures a hologram and an image of fluorescence emitted by a fluorescent material contained in the object, so that a superimposed image in which the hologram and the image of the fluorescence are superimposed is captured, the hologram formed by interference between reference light and object light from the object and reflecting a phase shift amount which varies across pixels and is determined by the reference light and the object light.

9. A digital holography device which includes the digital holography recording device according to claim 8 and a digital holography reconstruction device, the digital holography reconstruction device operable to:
use a spatial phase shift method to determine a complex amplitude of the object light based on the superimposed image in which (i) the hologram and (ii) the image of the fluorescence are superimposed;
determine an intensity of the hologram based on the complex amplitude of the object light; and
remove the hologram from the superimposed image to obtain the image of the fluorescence.

10. A digital holography device which includes the digital holography recording device according to claim 8 and a digital holography reconstruction device, the digital holography reconstruction device operable to:

subject, to Fourier transform, the superimposed image in which (i) the hologram and (ii) the image of the fluorescence are superimposed;

extract a spatial spectrum of the object light from a Fourier-transformed image;

subject the extracted spatial spectrum of the object light to inverse Fourier transform to determine a complex amplitude of the object light;

determine a zeroth-order diffracted light component based on the complex amplitude of the object light and then remove the zeroth-order diffracted light component from the Fourier-transformed image; and extract, from the Fourier-transformed image from which the zeroth-order diffracted light component has been removed, a spatial spectrum of the image of the fluorescence.

11. The digital holography device according to claim 10, wherein the image of the fluorescence is obtained by subjecting, to inverse Fourier transform, the extracted spatial spectrum of the image of the fluorescence.

12. A digital holography device which includes the digital holography recording device according to claim 8 and a digital holography reconstruction device, the digital holography reconstruction device operable to:

subject, to Fourier transform, the superimposed image in which (i) the hologram and (ii) the image of the fluorescence are superimposed;

extract a spatial spectrum of the object light from a Fourier-transformed image;

subject the extracted spatial spectrum of the object light to inverse Fourier transform to determine a complex amplitude of the object light; and determine an intensity of the hologram based on the complex amplitude of the object light and then remove the hologram from the superimposed image to obtain the image of the fluorescence.

13. A digital holography recording method comprising the steps of:

irradiating an object with object illumination light emitted from a light source so that object light is generated and exciting a fluorescent material contained in the object with the object illumination light; and simultaneously capturing a hologram and an image of fluorescence emitted by the fluorescent material, the hologram formed by interference between reference light and the object light and reflecting a phase shift amount which varies across pixels and is determined by the reference light and the object light.

14. A digital holography recording method comprising the steps of:

irradiating an object with object illumination light; and simultaneously capturing a hologram and an image of fluorescence emitted by a fluorescent material contained in the object, so that a superimposed image in which the hologram and the image of the fluorescence are superimposed is captured, the hologram formed by interference between reference light and object light from the object and reflecting a phase shift amount which varies across pixels and is determined by the reference light and the object light.

15. A digital holography method which includes the digital holography recording method according to claim 14, the digital holography method further comprising the steps of:

using a spatial phase shift method to determine a complex amplitude of the object light based on the superimposed image in which (i) the hologram and (ii) the image of the fluorescence are superimposed;

determining an intensity of the hologram based on the complex amplitude of the object light; and removing the hologram from the superimposed image to obtain the image of the fluorescence.

16. A digital holography method which includes the digital holography recording method according to claim 14, the digital holography method further comprising the steps of:

subjecting, to Fourier transform, the superimposed image in which (i) the hologram and (ii) the image of the fluorescence are superimposed;

extracting a spatial spectrum of the object light from a Fourier-transformed image;

subjecting the extracted spatial spectrum of the object light to inverse Fourier transform to determine a complex amplitude of the object light;

determining a zeroth-order diffracted light component based on the complex amplitude of the object light and then removing the zeroth-order diffracted light component from the Fourier-transformed image; and extracting, from the Fourier-transformed image from which the zeroth-order diffracted light component has been removed, a spatial spectrum of the image of the fluorescence.

17. A digital holography method which includes the digital holography recording method according to claim 14, the digital holography method further comprising the steps of:

subjecting, to Fourier transform, the superimposed image in which (i) the hologram and (ii) the image of the fluorescence are superimposed;

extracting a spatial spectrum of the object light from a Fourier-transformed image;

subjecting the extracted spatial spectrum of the object light to inverse Fourier transform to determine a complex amplitude of the object light; and determining an intensity of the hologram based on the complex amplitude of the object light and then removing the hologram from the superimposed image to obtain the image of the fluorescence.

* * * * *